(12) United States Patent
O'Neil

(10) Patent No.: US 7,335,186 B2
(45) Date of Patent: Feb. 26, 2008

(54) PATIENT CONTROLLED DRUG DELIVERY DEVICE

(75) Inventor: Alexander George Brian O'Neil, 102 Lawler St., Subiaco (AU) 6008

(73) Assignees: Alexander George Brian O'Neil, Subiaco (AU); Christine O'Neil, Subiaco (AU)

( * ) Notice: Subject to any disclaimer, the term of this patent is extended or adjusted under 35 U.S.C. 154(b) by 495 days.

(21) Appl. No.: 10/461,016

(22) Filed: Jun. 11, 2003

(65) Prior Publication Data

US 2004/0068222 A1  Apr. 8, 2004

Related U.S. Application Data

(63) Continuation-in-part of application No. 08/973,591, filed on Mar. 13, 1998, now Pat. No. 6,605,060.

(51) Int. Cl.
*A61M 1/00* (2006.01)

(52) U.S. Cl. .................................................... 604/152

(58) Field of Classification Search ............ 604/65–67, 604/151–153, 30, 31, 131; 293/303, 306; 222/380, 630, 321.1, 631, 387
See application file for complete search history.

(56) References Cited

U.S. PATENT DOCUMENTS

| 4,147,280 | A |   | 4/1979  | Spatz |
| 4,230,277 | A |   | 10/1980 | Tada .......................... 220/832 |
| 4,826,048 | A | * | 5/1989  | Skorka et al. .............. 222/137 |
| 4,828,551 | A |   | 5/1989  | Gertler et al. |
| 5,135,491 | A | * | 8/1992  | Baldwin ..................... 604/505 |
| 5,147,073 | A |   | 9/1992  | Cater ........................ 222/231 |
| 5,388,766 | A | * | 2/1995  | Buisson ..................... 239/333 |
| 5,389,078 | A | * | 2/1995  | Zalesky et al. ............. 604/151 |
| 5,527,288 | A | * | 6/1996  | Gross et al. ................ 604/140 |
| 6,605,060 | B1| * | 8/2003  | O'Neil ....................... 604/152 |

FOREIGN PATENT DOCUMENTS

| EP | 289856  | A1 | 11/1988 |
| EP | 342651  | A1 | 11/1989 |
| GB | 2084263 | A1 | 11/1983 |

(Continued)

*Primary Examiner*—Kevin C. Sirmons
*Assistant Examiner*—Catherine N. Witczak
(74) *Attorney, Agent, or Firm*—Fredrikson & Byron, P.A.

(57) ABSTRACT

A delivery device for patient-controlled infusion of a medicament, the delivery device comprising a reservoir for the medicament and a pump having a predetermined delivery dose which is capable of displacing the medicament from the reservoir and delivering it to a patient, wherein the pump comprises a pumping means, a first conduit, capable of restricting flow rate, chosen in conjunction with the delivery dose of the pumping means to define a predetermined maximum dosage rate, said conduit connecting the reservoir to a pumping means, a one-way valve in fluid communication with the first conduit and the pumping means which permits medicament flow into the pumping means but prevents reverse flow, a controlling means, and a second conduit extending from the pumping means and having a distal end through which the medicament may be released, wherein the controlling means: (a) is in fluid communication with the pumping means and the second conduit; (b) opens when pressured within the dose chamber exceeds a predetermined minimum opening pressure for the controlling means; and, (c) is adapted to prevent the reverse flow of medicament and air into the pumping means.

25 Claims, 13 Drawing Sheets

FOREIGN PATENT DOCUMENTS

| WO | WO 87/00758 A1 | 2/1987 |
| WO | WO 88/02637 A1 | 4/1988 |
| WO | WO 91/08002 A1 | 6/1991 |
| WO | WO 91/14468 A | 10/1991 |
| WO | WO 95/08400 A1 | 3/1995 |

* cited by examiner

PATIENT CONTROLLED DRUG DELIVERY DEVICE

CROSS REFERENCE TO RELATED APPLICATION

The present application is a continuation-in-part of U.S. patent application filed Mar. 13, 1998 and assigned Ser. No. 08/973,591 issued Aug. 12, 2003 as U.S. Pat. No. 6,605,060, the disclosure of which is incorporated herein by reference.

TECHNICAL FIELD

The present invention relates to an improved apparatus for effecting patient-controlled infusion of medicaments and is particularly applicable to the delivery of medicaments which may be absorbed across dermal and mucosal surfaces such as the respiratory tract, the nasal mucosa, the sublingual area, the ocular surface, intravaginal epithelium or intrarectal mucosa.

BACKGROUND ART

It has been recognized for some time that patient controlled medicament delivery (PCDD) as in the case of patient controlled analgesia (PCA) is desirable in many situations. Before the advent of patient controlled medicament delivery, therapeutic treatments relied upon periodic injections of medicaments such as natural and synthetic opioids by a physician or nurse. This has the disadvantage that for most of the time the patient's medicament level may be significantly above or below the optimum.

PCDD improved on the prior art by enabling the infusion of small quantities of medicaments at regular intervals as perceived to be required by the patient. However, to date PCDD has been effected by sophisticated electronic pump systems, which have a number of disadvantages:

(a) They are expensive;
(b) They are complex and require skilled maintenance; and
(c) They are capable of administering an overdose as a result of machine failure or of operator error in setting up; a number of deaths from this cause have been reported.

Recently mechanical PCDD pumping systems have been developed to ameliorate some of the disadvantages attendant with prior art devices. Such devices generally consists of a reservoir and a pumping assembly that contains a dose chamber which takes a predetermined amount of time to fill. These pumps have the disadvantage that filling of the dose chamber in the pumping assembly may take a long time and filling of the last portion of the dose chamber may be extremely slow. Moreover, if patients activate mechanical PCDD pumping systems prior to complete filling of the fluid dose chamber they may receive an excess of medicament. Thus, physicians may have no means of controlling the total amount of medicament delivered to a patient, leading to possible medicament overdosing by the patient.

Physicians generally associate the term "lockout" with a period of delay between medicament deliveries. They also have an expectation that the dose chamber in the delivery device will be 100% full at the end of each lockout period.

The filling cycle of electronic PCDD pumps is generally immediate. Electronic pumps allow a unit dose of medicament to be delivered and control a time interval where no further doses of medicament can be delivered. When this time interval is completed the patient can activate a switch which indicates his/her desire for another dose. The next unit dose will then be delivered and the next lockout will take effect.

In mechanical PCDD pumps the filling time of the dose chamber is progressive over a period of time that is equivalent to the predetermined lockout period. Typically, a concave filling curve is observed wherein the majority of the dose chamber fills rapidly after medicament delivery/release after which there is a slow and progressive filling of the last portion of the dose chamber. Often the filling time which leads to 100% filling of the dose chamber in such pumps is greater than the lockout period. Thus, a patient who activates the device prior to specified delivery times might obtain less than the absolute dose that is required to fill the dose chamber.

Depending on the type of PCDD pump employed, a patient may also gain significantly greater doses of a medicament than he/she should receive, by using the device at frequent intervals before the dose chamber is completely full. For example, a patient who activates a mechanical PCDD pump once every few minutes for an hour will gain significantly greater amounts of a medicament than they should receive if they use the pump once every 10 minutes over a 1 hour period. This is because the most rapid filling in mechanically controlled PCDD lockout pumps occurs in the first minutes. In some circumstances a patient may, for example, receive more than 200% of the expected dose of medicament if he/she activates the device at shorter time intervals than recommended for medicament delivery. This phenomenon has in the past led to patient overdose.

It has been found that by controlling the number of doses of a medicament that a patient receives per hour, it is possible to control many patient symptoms. In particular, patients can control their own symptoms by measuring the symptoms and adding doses of medicaments as required. In such situations physicians would choose the limit that will be an index of medicament safety for a certain dose to be delivered per hour.

The patient-controlled delivery device described in O'Neil et al (U.S. Ser. No. 08/973,591) provides a delivery device for patient-controlled infusion of a medicament, comprising a reservoir for the medicament and a pump having a predetermined delivery dose that is capable of displacing the medicament from the reservoir and delivering it to a patient. However, a problem that occurs with the O'Neil delivery device is that when the pump is tipped on its side, an air-fluid interface over the end of the suction tube may develop. This situation leads to air being sucked by the vacuum into the very fine bore tubing. The air within the tubing interferes with further functioning of the tubing. Thus, the presence of air in the tubing means that there is a reduction in the pressure gradient along the tubing and the resultant effect may be a failure of fluid to continue to flow along the tubing.

DISCLOSURE OF INVENTION

The present invention seeks to provide an improved PCDD apparatus which is simple and inexpensive to manufacture and use, and which has a high level of inherent safety. In addition, the present invention is directed towards a means to reduce the formation of a fluid-air interface occurring when the delivery device is in use.

The present invention provides a delivery device for patient-controlled infusion of a medicament, the delivery device comprising: (i) a reservoir for the medicament, which reduces in volume as medicament is withdrawn from the reservoir; and (ii) a pump which has a predetermined delivery dose, wherein the pump comprises at least a first conduit which connects the reservoir to a pump chamber, a one-way valve in fluid communication with the first conduit and the pump chamber which permits medicament flow into the chamber but prevents reverse flow there from, a second conduit extending from the pump chamber and having a distal end through which the medicament may be released, and a controlling means in fluid communication with said pump chamber and said second conduit, wherein:

(a) the first conduit is a fine calibre tube, which is capable of restricting the filling time of the pump chamber to greater than 1 minute, and is suitably adapted to restrict the flow of medicament into the chamber to a predetermined maximum delivery rate;

(b) the controlling means:
  (i) opens when pressure within the pump chamber exceeds a pre-selected minimum opening pressure, said opening pressure being greater than 760 mmHg;
  (ii) is adapted to prevent the reverse flow of medicament and air into the pump chamber; and (c) the second conduit is adapted to release the medicament in the form of a spray;

wherein after expulsion of medicament from the pump chamber a working interrelationship is formed between the fine calibre tubing and the controlling means to generate a lockout phase during which a patient is unable to effectively access a dose of medicament being drawn into the pump chamber until said chamber contains sufficient medicament to aid in treating said patient.

The present invention attempts to minimize the potential for patients to overdose with medicaments by providing a physical lockout time delay between one dose and the next. This delay is created by developing a working interrelationship between the first conduit, the pumping means and the controlling means. The first conduit restricts the passage of medicament into the dose chamber thereby providing the dose chamber with a predetermined filling time. In combination there is provided a controlling means that is adapted to retard the release of medicament from the dose chamber until a suitable opening pressure (driving force) can be generated in the dose chamber to open the controlling means. Thus a more efficient lockout may be created whereby a patient is prevented from obtaining additional doses of a medicament from the delivery device until the chamber contains a suitable dose of spray to treat said patient's ailment.

The first conduit is preferably a fine calibre tube that has a very narrow bore and which limits the filling time of the dose chamber to between 1 minute and 12 hours. The desired time delay for filling the dose chamber would depend on a variety of factors such as the concentration of medicament to be delivered by the delivery device, the physical properties of the medicament, the delivery route, the delivery volume and the number of times that the medicament is to be delivered per day. Preferably, the time delay is between 1 minute and 10 hours. More preferably the time delay is greater than 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 18, 19, 20, 25, 30, 35, 40, 45, 50, 55 or 60 minutes, but less than 10, 9, 8, 7, 6, 5, 4, 3, 2 hours or less than 110, 100, 90, 80, 70, minutes. In one highly preferred form of the invention the time delay is between 10 to 20 minutes. For example, the time delay may be 15 minutes.

Any fine calibre tubing that is able to limit the flow rate of medicament into the dose chamber to a desired fill time may be used in the invention. Such a tube and a method for producing it are described in co-owned international patent application WO88/02637. Preferably, the tube is less than 700 cm in length. More preferably the tube is less than 650, 600, 550, 500, 450, 400, 350, 300, 250, 200, 150, 100, 90, 80, 70, 60, 50, 40, 30, 20, 10, 9, 8, 7, 6, 5, 4, 3, 2 or 1 cm. Further, the tube should also be substantially resistant to kinking and will generally have a lumen diameter of about 0.001 mm to 1 mm. More preferably the lumen diameter will be between 0.09 and 0.2 mm or between 0.08 and 0.5. Desirably the diameter of the lumen will be around 0.05 and 0.8. For example, nasal spray apparatuses for the delivery of fentanyl which employ fine calibre tubing that have a lumen diameter in the range of 0.003 of an inch (0.025 mm) and a length of approximately 9 cm give a filling time of approximately 5 minutes with a dose chamber of 0.2 ml (200 μl).

The fine calibre tubing employed in the invention has a fine calibre bore, which consequently makes it difficult to prime the apparatus. In order to alleviate this potential problem preferably the fine calibre tubing is connected to the pumping means by a releasable engaging means. Accordingly the tubing is separable from the pumping means to facilitate priming and or the attachment of other fine calibre tubings with alternative specifications.

Preferably the controlling means is biased towards the closed position but is capable of allowing fluid flow in one direction while restricting or more preferably preventing the reverse flow of fluid. In a highly preferred form of the invention the controlling means may be a one-way ball, disc or elastomeric type valve or as a two part plunger wherein the parts are biased together by a resilient biasing means (such as a spring or a deformable rubber or rubber like support) and which is opened by separation of the plunger parts.

The controlling means is preferably positioned in conjunction with the second conduit and is activated only under high pressure. For example, the opening pressure of the controlling means should be greater than 760 mmHg so that all fluid leaving the dose chamber leaves under high pressure thus facilitating atomisation of the medicament as it leaves the second conduit. Preferably the controlling means has an opening pressure in the order of 760 mmHg to about 5000 mmHg. In a more preferred form a pressure of about 1000 mmHg to about 3500 mmHg would be a typical opening pressure with about 3000 mmHg being optimal for the controlling means. Any controlling means which opens when a predefined pressure is reached may be used in the invention.

Once fluid has started to move through the controlling means the pressure required to maintain the controlling means open will preferably be much lower than the initial opening pressure. Means for achieving this end are known in the art.

By employing a high pressure controlling means in the pumping assembly it is possible to restrict a patient's access to small partial doses of medicament present in a delivery device during the phases of most rapid filling. If the controlling means has a high opening pressure, a patient will generally have great difficulty generating suitable opening pressures when the chamber contains a small amount of medicament and a large vacuum. The mechanical pressure required to generate a high opening pressure while pressing a vacuum against a medicament makes it exceptionally difficult, if not impossible, to release any medicament in a suitable form from the pumping assembly unless mechanical assistance is given to the patient's hand. The abound of mechanical assistance that may be given to the patient's hand may be controlled by the size, diameter and length of the dose chamber and the configuration of the mechanism that allows pressure to be applied to the device. Means for achieving this end are known in the art.

The effect established by employing a working interrelationship between the fine calibre tubing and the controlling means is characterized by the inability of a patient to obtain an effective dose of medicament during the lockout period. Post release of medicament from the dose chamber there is a phase of rapid filling of the chamber. Throughout this phase, medicament is prohibited from release in an effective amount from the device because there is insufficient pressure in the dose chamber to force open the high pressure controlling means.

As the volume of medicament in the dose chamber increases the pumping means may become capable of generating a suitable pressure to open the controlling means. However, because all of the energy exerted on the medicament is utilized in opening the controlling means there is insufficient positive pressure generated in the dose chamber to drive the fluid through the second conduit. Thus, any medicament released from the device quickly coalesces to form fluid droplets at the apex of the second conduit. Thus, medicament is not released from the device.

As the dose chamber reaches about three quarters full the pressure that may be generated therein should start to become sufficient to force the controlling means to open and drive fluid through the second conduit. Thus, medicament may be released from the device. However, because most of the energy (driving force) created upon activation of the device is used to open the controlling means the force driving the spray is relatively low. The released spray quickly coalesces as it leaves the dose chamber. Absorption of the medicament into the dermal or mucosa surrounding the region of medicament delivery is retarded because only a small surface area of tissue comes into contact with the medicament. The quantity of medicament absorbed is proportional to the size of the dermal or mucosal surface that is saturated with the medicament.

When the dose chamber becomes full, maximum pressure can be generated in the dose chamber upon compression of the pump. The droplet size of the medicament decreases as the pressure generated in the dose chamber increases. The decreasing size of droplets and increasing size of the spray allows the medicament to reach the whole of the dermal or mucosa surface that is to be saturated by medicament release. Thus, allowing maximum absorption of a unit dose of medicament.

A preferred feature of the present invention resides in the provision of a means for reducing the medicament to fine particles by atomising it or nebulising it as it passes through the second conduit. To achieve this, fluid is preferably pumped under high pressure up the sidewalls of the second conduit, preferably in a rotary action. Such an action may, for example, be achieved by forming groves in the inner walls of the conduit, which facilitate rotary movement of fluid therein. The conduit is preferably made narrow towards its distal end so that fluid rotating around the conduit increases its centrifugal rotation as it converges on the aperture at the distal end of the conduit. The high centrifugal force causes the fluid emerging from the aperture to break into fine droplets.

The droplet size is determined by the rate of flow through the first conduit, the pressure pushing the fluid up the conduit, the amount of rotation that has been achieved as the fluid moves up the conduit, the amount of convergence at the distal end of the conduit as it narrows into the aperture and the viscosity of the fluid itself. If the invention is employed to deliver a nasal spray, the droplet size may be decreased by increasing the opening pressure of the controlling means. An increase in opening pressure of the controlling means also helps to produce a greater time delay.

Any pumping means that is able to draw medicament through a first conduit and discharge a defined volume of it through a second conduit may be used in the delivery device. Preferably the pumping means has a dose chamber into which medicament is drawn and from which it is expelled. The dose chamber preferably defines the volume of medicament that is drawn into and expelled from the pumping means. A dose chamber with a low unit dose size is preferably employed in the pumping means so that manual pressure applied without any levers or complex devices by a patient is capable of generating high pressures inside the dose chamber. This usually means that the chamber must be small and have a small diameter such that a patient may be able to generate pressures above several thousand millimeters of mercury within the dose chamber to open a controlling means. Desirably the dose chamber will be between 10 to 1000 μl. More preferably the dose chamber will be between 30 to 800 μl. Even more preferably the dose chamber will be between 50 to 500 μl. By way of illustration only, for nasal sprays a typical unit dose size may be 50 to 250 μl. In this respect clinical studies performed by the inventor have established that 120 to 160 μl nasal sprays of Fentanyl at a concentration of 150 to 900 μg per ml of Fentanyl is a highly effective delivery dose.

The pumping means may be of any form that is capable of withdrawing medicament through fine calibre tubing and then displacing it under high pressure through a second conduit. For example, the pumping means may be a syringe-type design having a plunger biased upwardly within the dose chamber by a resilient restoring means wherein depression of the plunger provides the means for volume reduction and displacing the medicament in the dose chamber. Such a pump is described in European patent application EP 0301615 in the name of Elettro Plastica s.r.l.

If, for example, the pump takes the form of a syringe-type pump the delivery device may be actuated by the user to deliver a fixed dose of medicament by applying pressure to the pump plunger. This forces medicament from the dose chamber through the second conduit which preferably atomises/nebulises the medicament as it passes from the delivery device. A resilient restoring means in the dose chamber then returns the plunger to its resting state thereby reforming the dose chamber. This creates a vacuum in the dose chamber that displaces the one-way valve and draws fluid from the reservoir through the first conduit (e.g. fine calibre tube) refilling the dose chamber.

For some medicaments a limit of 2-3 doses per day with delays as long as 6 to 8 hours may be required. It will be appreciated that the administration volume and the time delay between deliveries may be varied by altering, for example, the calibre and/or length of the first conduit and the volume in the dose chamber.

If, for example, the pumping means is of a syringe-type design the resilient restoring means may be a spring. The return pressure of the spring should be sufficient to return the syringe mechanism to its pre-activation state while drawing fluid into the dose chamber by the creation of a vacuum in said chamber. Preferably, the spring is adapted in such a way that at the beginning of pressing the syringe plunger, the pressure on the spring is minimal and as the movement continues the spring pressure increases. When the pressure exerted by the spring is significant it may be very difficult for a patient to express the last part of the fluid unless a high opening pressure in the controlling means has been overcome.

Preferably, the return spring on the plunger is relatively short such that the pressure required to activate the device is low when the chamber is full, medium when the chamber is half full and extremely high when the chamber if full of small quantities such as 10 or 20%. When such a spring is combined with a high pressure controlling means it becomes very difficult to deliver a dose from the dose chamber except when it is full to a significant amount. By altering the balance of pressure exerted by the spring pressures on the return spring driving up the plunger and the inertia pressures on the controlling means it is possible to vary control of medicament release from the initial part of the dose chamber so that expulsion of fluid from it becomes impossible until a desired quantity of fluid has entered the dose chamber.

Alternatively the syringe-type pump may be replaced by a balloon or a concertina type pumping mechanism. In these forms activation of the pump may be achieved by compression of the balloon or concertina mechanism to create a pressure change within the dose chamber. The balloon or concertina mechanism is preferably a thick-walled rubber balloon or concertina mechanism with sufficient recovery force to draw medicament from the reservoir through the first conduit.

Preferable the one-way valve is engaged to either the first conduit or is located between the first conduit and the dose chamber. Without the presence of the one-way valve the small volumes involved with nasal sprays and the pressure of the operating system would create a back flow of fluid through the first conduit. The valve may be, for example, spring, ball or elastomeric activated valve.

The second conduit may be of any length or diameter. Preferably its length and diameter are adapted to suit the orifice or dermal region for which medicament delivery is intended. For example, if medicament delivery is intended for the nasal mucosa or the respiratory tract via the nasal cavity then the second conduit may be short and of a suitable diameter to fit the nostril(s) of a patient. Alternatively, if medicament delivery is intended for the rectal or vaginal mucosa then the second conduit may be comparatively longer and of a wider diameter.

The second conduit may also be sheathed. If the conduit is sheathed then the distal end of the sheath must contain at least an orifice through which medicament can pass as it is released from the delivery device. The sheath may be disposable or a permanent fixture engaged with the delivery device. The sheath may also serve as a means for actuating the pump. For example, if the pump is a syringe-type pump the sheath may partially cover the plunger and may have one or more perpendicular extensions that allow the user to depress the plunger. If however, the pump is an elastomeric balloon then the sheath may serve only as a means for protecting the second conduit.

The reservoir employed in the invention may take any form or contain any volume of medicament. Preferably the reservoir is a chamber that reduces in volume as liquid is withdrawn from the reservoir. For example the reservoir may be a collapsible bag or a syringe that is (i) adapted to engaged the pump, (ii) is capable of holding the length of the first conduit and (iii) reduces in volume as the fluid is removed thereby reducing the occurrence of a fluid-air interface forming.

Where the reservoir is a collapsible bag, the bag may be made from any suitable material that does not absorb significant quantities of medicament. In particular, where the medicament is a lipaphyllic drug the bag should be made of a material that does not soak-up the lipaphyllic drug used with the delivery device. Suitable materials include: polyethylene, polyethylene lined components, teflon or like materials. Preferably the bag is made from polyethylene or a polyethylene like material. Further, the collapsible bag may be of any size suitable for incorporating in the delivery device. However, restricting the size of the bag containing medications offers an important safety aspect. For practical purposes the collapsing bag may be limited to a small volume. For example, a bag limited to a small volume such as 2 ml of fluid limits the use of a 0.2 ml dose to ten specific doses. The small size of the bag containing an analgesic drug or other solution minimizes the risk of overdose in the event of tampering with the container. It is therefore appropriate in many clinical situations that the size of the bag containing the fluid is kept small to minimize the risk of overdose when tampering occurs.

Where the reservoir is prepared in the form of a deformable bag, the bag will preferably be protected by a reservoir body that engages, preferably in a releasable manner, the pump housing. Thus in one embodiment, the reservoir body is a relatively narrow necked container with a phalange and a wide brim. This is connected to a routine crimping cap prior to connecting the collapsible bag to the pump housing. The part of the container that covers the bag can be glued onto the upper portion of a container attached to the crimped fitting holding the pump housing. This two component bottle or fitting replaces the traditional bottle used on nasal spray devices and facilitate manufacturing of a collapsible bag that holds fluid for the delivery device.

An alternative reservoir is a syringe with a plunger arrangement that reduces in volume as fluid is removed from the syringe chamber.

If the reservoir is in sealing engagement with the pump, there may be provided in the wall of the reservoir one or more means for introducing a medicament into the reservoir. If the reservoir is provided with a delivery portal for introducing medicament into the apparatus, there is preferably provided a means for trapping gases to prevent air inadvertently introduced at the injection site from reaching the reservoir. Alternatively, a release portal may be provided for removing from the system air either introduced inadvertently or in the initial purging of the system.

In a second embodiment of the invention there is provided a delivery device for patient-controlled infusion of a medicament, the delivery device comprising: (i) at least a first and second reservoir for medicament storage; and (ii) a pump which has a predetermined delivery dose, wherein the pump comprises a separate conduit feeding into each reservoir to connect said reservoir to the pump chamber, a one-way valve in fluid communication with each conduit extending from the reservoir and the pump chamber which permits medicament flow into the chamber but prevents reverse flow there from, a second conduit extending from the pump chamber and having a distal end through which the medicament may be released, and a controlling means in fluid communication with said pump chamber and said second conduit, wherein:

(a) Each conduit connecting the reservoir to the dose chamber is a fine calibre tube, which is capable of restricting the filling time of the pump chamber to greater than 1 minute, and is suitably adapted to restrict the flow of medicament into the chamber to a predetermined maximum delivery rate;

(b) the controlling means:
  (i) opens when pressure within the pump chamber exceeds a pre-selected minimum opening pressure, said opening pressure being greater than 760 mmHg;
  (ii) is adapted to prevent the reverse flow of medicament and air into the pump chamber; and
(c) the second conduit is adapted to release the medicament in the form of a spray;

wherein after expulsion of medicament from the pump chamber a working interrelationship is formed between the fine calibre tubing and the controlling means to generate a lockout phase during which a patient is unable to effectively access a dose of medicament being drawn into the pump chamber until said chamber contains sufficient medicament to aid in treating said patient.

According to this embodiment there is provided a plurality of conduits each feeding medicament from a single reservoir into the dose chamber. In this configuration two or more medicaments may be mixed in the dose chamber before being delivered to the patient, Moreover because the medicaments are not mixed until entry into the dose chamber possible chemical interaction between the two different medicaments may be kept to a minimum.

The device encompassed in the second embodiment is not limited to delivery of two medicaments in equal proportions. In this respect the relative ratio of the medicaments mixed in the dose chamber may be varied by altering the properties (eg length of the conduit, the lumen diameter) of the conduit feeding medicament and or the viscosity of the medicament that is transferred via the conduit from the reservoir to the dose chamber.

Preferably, medicament is stored in a reservoir that reduces in volume as medicament is withdrawn from the reservoir.

In a third embodiment of the invention there is provided a delivery device for patient-controlled infusion of a medicament, the delivery device comprising: (i) at least a first reservoir for medicament storage; and (ii) a pump which has a predetermined delivery dose, wherein the pump comprises a conduit feeding from each reservoir to connect said reservoir to the pump chamber, a second conduit extending from the pump chamber and having a distal end through which the medicament may be released, and a controlling means in fluid communication with said pump chamber and said second conduit, wherein:
  (a) Each conduit connecting the reservoir to the dose chamber is a fine calibre tube, which is capable of restricting the filling time of the pump chamber to greater than 1 minute, and is suitably adapted to restrict the flow of medicament into the chamber to a predetermined maximum delivery rate;
  (b) the controlling means:
    (i) opens when pressure within the pump chamber exceeds a pre-selected minimum opening pressure, said opening pressure being greater than 760 mmHg;
    (ii) is adapted to prevent the reverse flow of medicament and air into the pump chamber; and
  (c) the second conduit is adapted to release the medicament in the form of a spray;

wherein after expulsion of medicament from the pump chamber a working interrelationship is formed between the fine calibre tubing and the controlling means to generate a lockout phase during which a patient is unable to effectively access a dose of medicament being drawn into the pump chamber until said chamber contains sufficient medicament to aid in treating said patient.

In the absence of a one-way valve transposed in the conduit between the reservoir and the dose chamber, fluid may be driven down the conduit when pressure is applied to the dose chamber to force medicament there from. In such situations preferably the bore of the lumen is kept to an absolute minimum such that the narrow bore provides resistance to the fluid flowing through it, which resistance is less than that required to open the controlling means. Alternatively, the portal through which medicament may flow to enter the dose chamber may narrow or contain one or more flanges which serve to restrict the size of the portal, therein adding a means to resist the reverse flow of fluid. Thus upon actuation of the device fluid will preferentially leave the device through the second conduit rather than through the conduit through which the medicament was initially drawn.

In a fourth embodiment of the invention the reservoir may be connected to the delivery device via a fluid control system, comprising: (i) a second reservoir which holds a small number of medicament doses which is located between the end of the flow control tubing and the delivery device; (ii) a fluid delivery means interposed between the reservoir and the second reservoir; and (iii) a high pressure activated valve with an opening pressure above atmospheric pressure which is interposed between the fluid delivery means and the second reservoir, wherein the fluid delivery means is capable of drawing medicament through the flow control tubing, is capable of holding a volume of medicament equivalent to the volume held by the second reservoir and is capable of delivering that medicament across the a high pressure activated valve to the second reservoir. A typical opening pressure for the high pressure activated valve would be above 800 mmHg ensuring that even with a full vacuum pressure transferred to the valve, that no fluid will flow cross the valve as the opening pressure is above atmospheric pressure (760 mmHg). In this embodiment the maximum number of doses that can be delivered to the patient is defined by the number of doses held in the second reservoir.

Any fluid delivery means may be used in this embodiment of the invention. For example, the fluid delivery means may be an electronic or non-electronic pump system or an aspirating syringe etc. If, for example, the fluid delivery means is an aspirating syringe and is attached to the reservoir by flow controlling tubing the time for filling the aspirating syringe is controlled by the rate of flow across the flow control tubing. Once the aspirating syringe is full, it may be activated to discharge its contents across the high pressure valve to the second reservoir. The delivery device can then be used to withdraw medicament from the second reservoir to fill the dose chamber prior to delivery to a patient without the need for flow control tubing between the delivery device and second reservoir. The number of doses available to the patient is determined by the number of doses in the second reservoir. Preferably, a patient is able to re-prime the second reservoir at a rate controlled by the flow control tubing that controls the rate of fill of the dose chamber. In this embodiment a patient could delivery 3, 4, 5, 6 or whatever number of doses are necessary in order to get the desired clinical effect but the dose number would be limited by the volume of the small reservoir.

In an alternative embodiment the main reservoir may be pressurized. (i.e., a spray can). Fluid is then pushed through the flow control tubing to the unit dose reservoir.

In another embodiment of the present invention there may be provided a secondary delivery control assembly that is releasable engaged to the second conduit, to facilitate control of fluid delivery. The secondary delivery control assembly comprising (i) a second delivery chamber, (ii) a return tube to the reservoir and (iii) an intravenous delivery line. The return tube preferably extends from the second delivery chamber to the reservoir bottle and facilitates the return of medicament released into the second delivery chamber that is incapable of entering the intravenous delivery line. Within the housing of the second delivery chamber there is provided an air filter to remove trapped air and a delivery portal within which there is located a second pressure activated controlling means. Connected to the delivery portal in a releasable manner is the intravenous delivery line that may be connected to a patient.

In use, when a high pressure dose of medicament is released into the second delivery chamber from the delivery device the pressure driving the dose out of the delivery device forces open the second pressure activated controlling means enabling the medicament to pass through the intravenous delivery line to the patient. However, when a low-pressure dose enters the second dose chamber the energy driving the dose is insufficient to activate the second pressure activated controlling means. In such circumstances fluid returns to the reservoir via the return tube to the reservoir.

Patient controlled delivery of medicaments that have a rapid action of onset may be delivered onto any dermal or mucosal surface that absorb medicaments quickly. Examples of surfaces that absorb medicaments quickly include the ocular surface, the respiratory tract, the nasal mucosa, the sublingual surface, the vaginal mucosa and the rectal mucosa. Preferably the route of delivery is dictated by the pharmokinetic properties of the medicament that is being delivered.

A typical intranasal medicament dose might be between 1 and 300 μL while doses used for applying medicaments to skin or modified skin such as vagina or rectum may be significantly larger. The following represents a list of some of the medicaments which may be used with the apparatus of the present invention:

1. Drugs affecting the alimentary tract
   (i) $H_2$ Receptor Antagonists: A large group of receptor $H_2$ antagonists may be delivered intravenously to control symptoms. They may also be delivered hourly, they could also be delivered by intra-nasal delivery virtually as a constant infusion to control symptoms from ulcers. Examples include: Famotidine, Cimetidine and Ranitidine Hydrochloride.
   (ii) Gastrointestinal tract—antispasmodics such as Hyoscine Butylbromide and Hyoscine Hydrobromide.
   (iii) Cardiovascular medicaments such as Methyldopate HCl, Hydralazine hydrochloride, Clonidine hydrochloride, Verapamil, Glyceril Trinitrate, and Diazoxide and Sodium nitroprusside.
   (iv) Cardiovascular medicaments—Beta-adrenergic blocking agents such as: Esmolol hydrochloride, Propranolol HCl and Atenolol.
   (v) Cardiovascular medicaments with diuretic effects such as Frusemide.
   (vi) Cardiovascular medicaments—anti-arrhythmic agents such as: Amiodarone hydrochloride, Verapamil hydrochloride, Procainamide hydrochloride, Disopyramide, Flecainide acetate, and Lignocaine hydrochloride.
   (vii) Cardiovascular medicaments—anti-angina agents such as: Glyceryl trinitrate.
   (viii) Cardio-ionatropic agents such as Digoxin
   (ix) Adrenergic stimulants such as: Adrenalin, Metaraminol bitartrate, Dobutamine hydrochloride, Isoprenaline hydrochloride, Noradrenaline acid tartrate and Dopamine hydrochloride.
   (x) Antimigraine preparations such as: Dihydroergotamine mesylate, and Sumatriptan succinate.
   (xi) Other cardiovascular agents such as: Indomethacin.
2. Central nervous system medicaments
   (i) Sedatives and Hypnotics such as: Chlormethiazole, Midazolam, Paraldehyde and Propofol.
   (ii) Anti-anxiety agents such as: Diazepam, Droperidol, Chlorpromazine hydrochloride, Haloperidol decanoate, and Chlorpromazine hydrochloride.
3. Movement disorders such as Benztropine mesylate, Phenytoin sodium, Phenobarbitone sodium and Clonazepam.
4. Narcotic analgesics such as Fentanyl citrate, Sufentanyl, Alphentanyl, Morphine Sulphate, Pethidine hydrochloride, Phenoperidine hydrochloride, Papaveretum, Methadone hydrochloride, Buprenophine hydrochloride, Hydromorphine, Dimorphine and Remifentanil.
5. Non-steroidal agents such as Indomethacin, Naproxen and Ketorolac trometamol.
6. Hormonal preparations such Menopausal Gonadotrophin, Growth Hormone—Somatropin, Desmopressin acetate, Bromocriptine mesylate, Octreotide, Insulin, Glibenclamide, Metformin hydrochloride, Glipizide and Tolbutamide.
7. Agents acting on the uterus such as: Oxytocin.
8. Prostaglandins such as Ritodrine hydrochloride and Salbutamol sulfate.
9. Bronchospasm relaxants such as Aminophylline, Theophylline, Salbutamol sulfate, Orciprenaline sulfate, Ipratropium bromide, Fenoterol hydrobromide, Terbutaline sulfate and Adrenaline acid tartrate.
10. Other peptides and proteins.
11. Lipophilic opiates such as Fentanyl, hydromorphine, diamorphine, pethidine.
12. Hydrophilic blockers such as Naloxone
13. Combination of Lipophilic opiates and hydrophilic blockers such as Naloxone/Fentanyl, Naloxone/hydromorphine, naloxone/diamorphine, naloxone/pethidine.

The above list of medicaments that may be applied in a rate controlled manner using the present invention is not an exhaustive list. These are specific medicaments which may have maximum hourly infusion rates that need to be prescribed by a physician to maintain patient safety. Preferably any medicament that might be given by continuous intravenous infusion or by a patient controlled intravenous infusion can be potentially delivered using the present invention.

The present invention is not limited to the delivery of a single medicament from the reservoir. That is more than one medicament may be administered at the same time using the delivery device of the present invention. Usually this will be achieved by mixing the two medicaments either in the reservoir or prior to administration to the reservoir. Where two or more medicaments are coadministered the two medicaments will be prepared in a form permitting each to be miscible in the other. Means for achieving this will be known in the art. Preferably the two medicaments will be prepared in a manner and in a form that minimizes the separation of the two medicaments. Further, preferably the two medicaments will be selected to minimize any counteractive interaction between the medicaments.

For example to enhance safety for patients, a hydrophilic blocker may be mixed with a lipophylic drug. When these two chemicals are delivered through the device of the present invention, the hydrophilic blocker is not absorbed across the nasal mucosa, whereas the lipophylic drug is absorbed across the mucosa. A mixture of hydrophilic blocker and lipophylic drug prevents misuse of the lipophylic drug. That is, an individual is prevented from overdose if the solution is injected intravenously as the hydrophilic blocker will block the lipophylic drug and especially the peak dose of the lipophylic drug when delivered intravenously.

This is especially so when the half-life of the lipophylic drug is similar to the half-life of the hydrophilic blocker. In a preferred embodiment, the typical 2 ml volume of the solution would include 600 µg of lipophylic drug (300 µg/ml) and 400 µg (200 µg/ml) of hydrophilic blocker. Even when the ratio of the solution contains a low concentration of hydrophilic blocker, such as 20 µg/ml, safety of drug administration is still achieved.

Any hydrophilic blockers known to those skilled in the art may be used to improve safety of the device. Hydrophilic blockers include—naloxone. In a highly preferred embodiment the hydrophilic blocker is Naloxone.

Any lipophylic drug, including lipophylic opiates may be used in the device of the present invention. Other lipophylic drugs include fentayl, hydromorphine, diamorphine, pethidine. In a highly preferred embodiment, the lipophylic drug is Fentanyl.

A risk associated with patient-controlled delivery devices is that other patients for whom the device was not intended may use it. Therefore, in a further embodiment of the present invention, a chain or string may be attached to the device so that it can be hung around the patient's neck, thereby minimizing the risk of being used by patients for whom it was not intended. Any mechanism of attaching the device to the patient which minimizes the risk of the device being left around in a place where non-authorised use of the device might occur may also be used.

In yet a further embodiment of the present invention, a counter may be added to the delivery device which allows the number of uses of the nasal spray to be recorded. This has the advantage of making the nasal spray considerably easier for nursing and medical staff to record and monitor administration of drugs used in the device.

It will be understood that there may be modifications and changes to the present invention that will be apparent to one skilled in the art upon reading this specification. These modifications and changes are to be encompassed in the scope of the present invention.

BRIEF DESCRIPTION OF THE DRAWING

The present invention will now be described by way of example only, with reference to the accompanied drawings in which.

BEST MODE OF CARRYING OUT THE INVENTION

Figure 1:
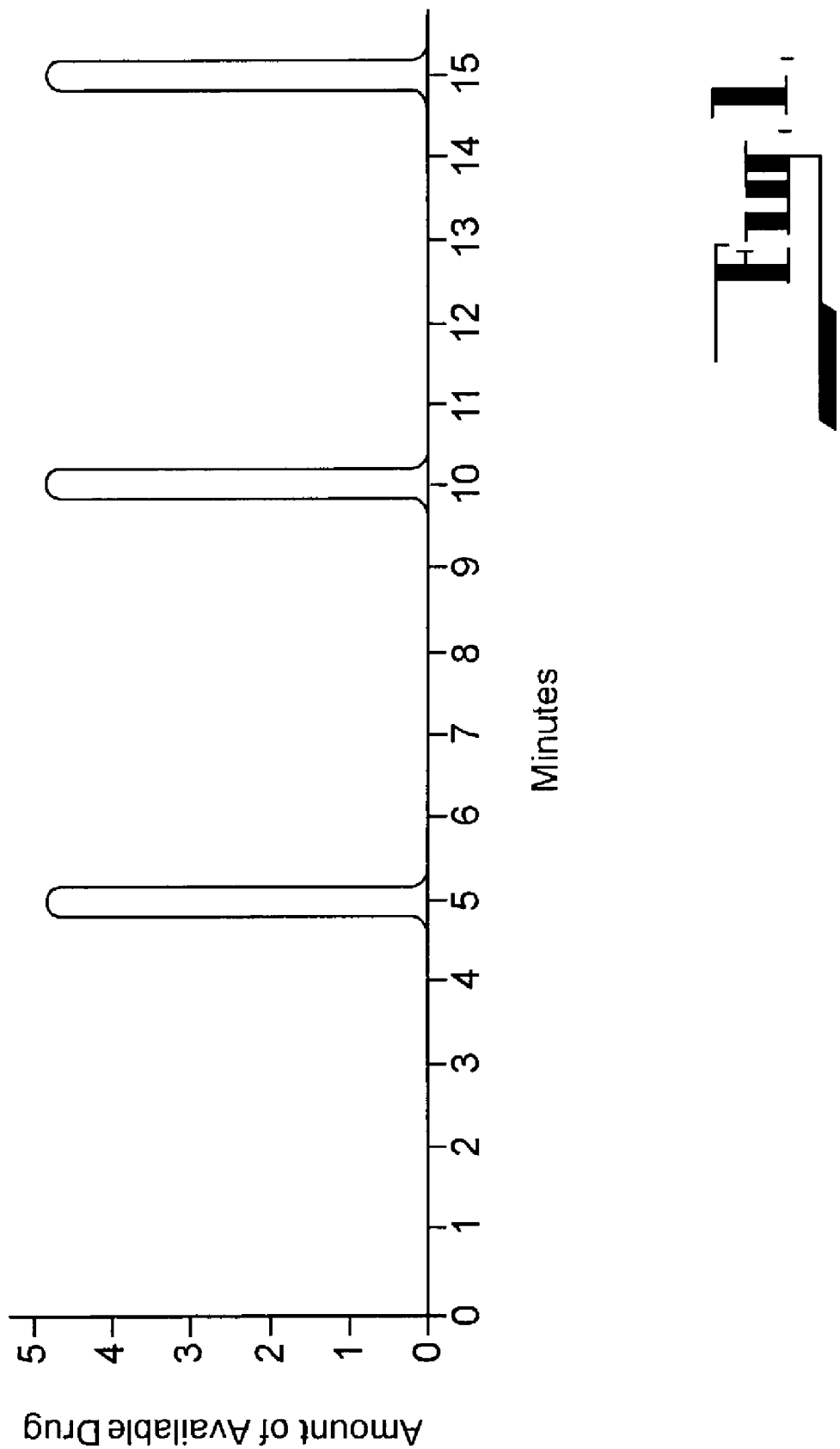
FIG. 1 shows the medicament filling and availability curve for an electronically driven pumping means.

FIG. 1 illustrates a typical prior art type medicament filling and availability curve for an electronically driven pumping system. Drug availability is only accessible once every 5 minutes in a 5 minute delivery schedule. Departure from the delivery schedule is prohibited by electronic locks which prevent access to the medicament.

Figure 2:
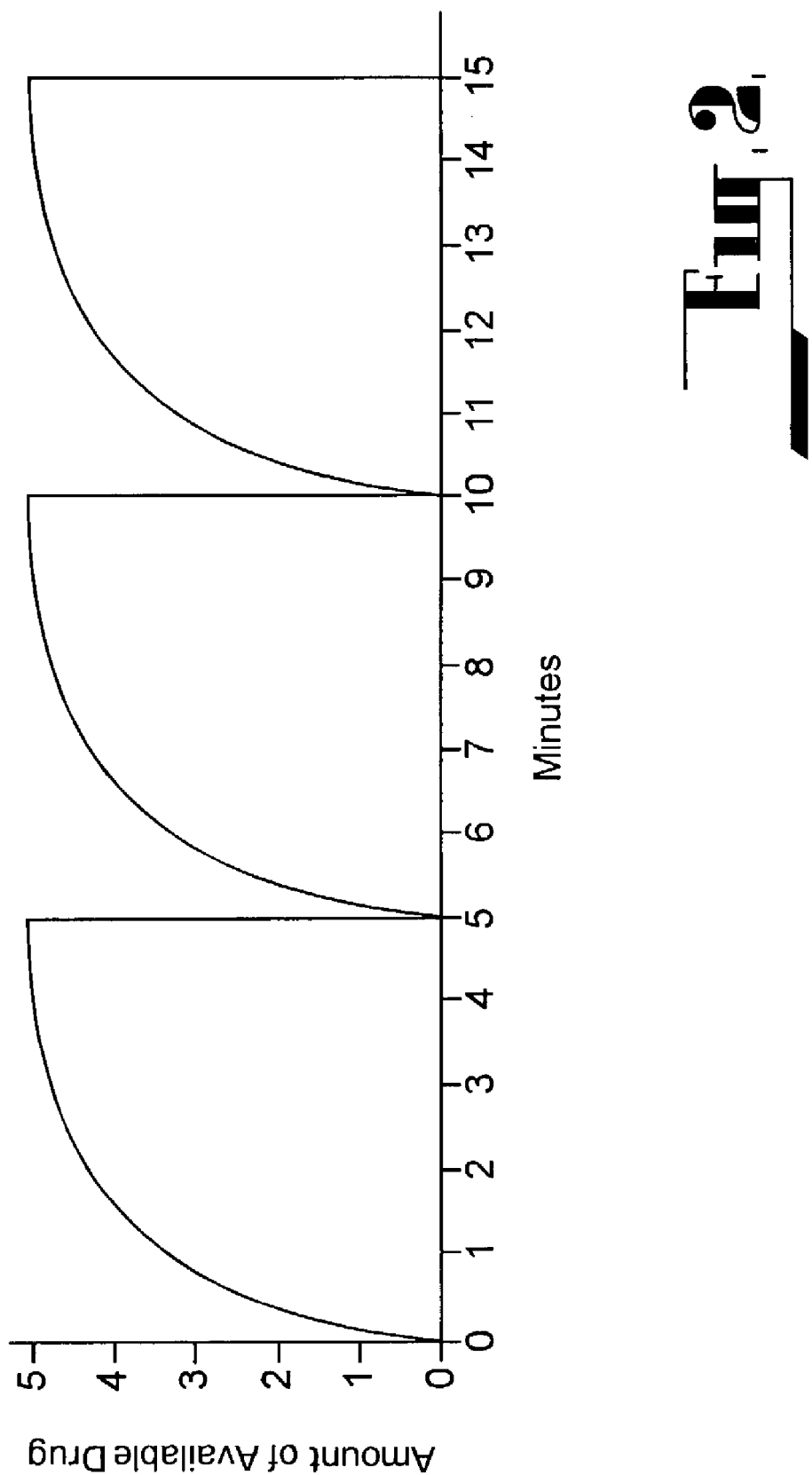
FIG. 2 shows the filling curve for a 5 minute intravenous vacuum driven PCA pump.

FIG. 2 illustrates a typical prior art type medicament filling and availability curve for a vacuum driven PCDD pump. The curve represents the filling time of the dose chamber followed by medicament delivery in a 5 minute delivery schedule. Provided the patient does not depart from the delivery schedule 100% of the medicament will be delivered every 5 minutes. However, if a patient attempts to obtain access to the medicament before the scheduled 5 minute filling time is completed, he/she may obtain significant amounts of the medicament at 1, 2, 3 and 4 minutes post delivery of the previous administration. This may lead to an overdose of the medicament.

Figure 3:
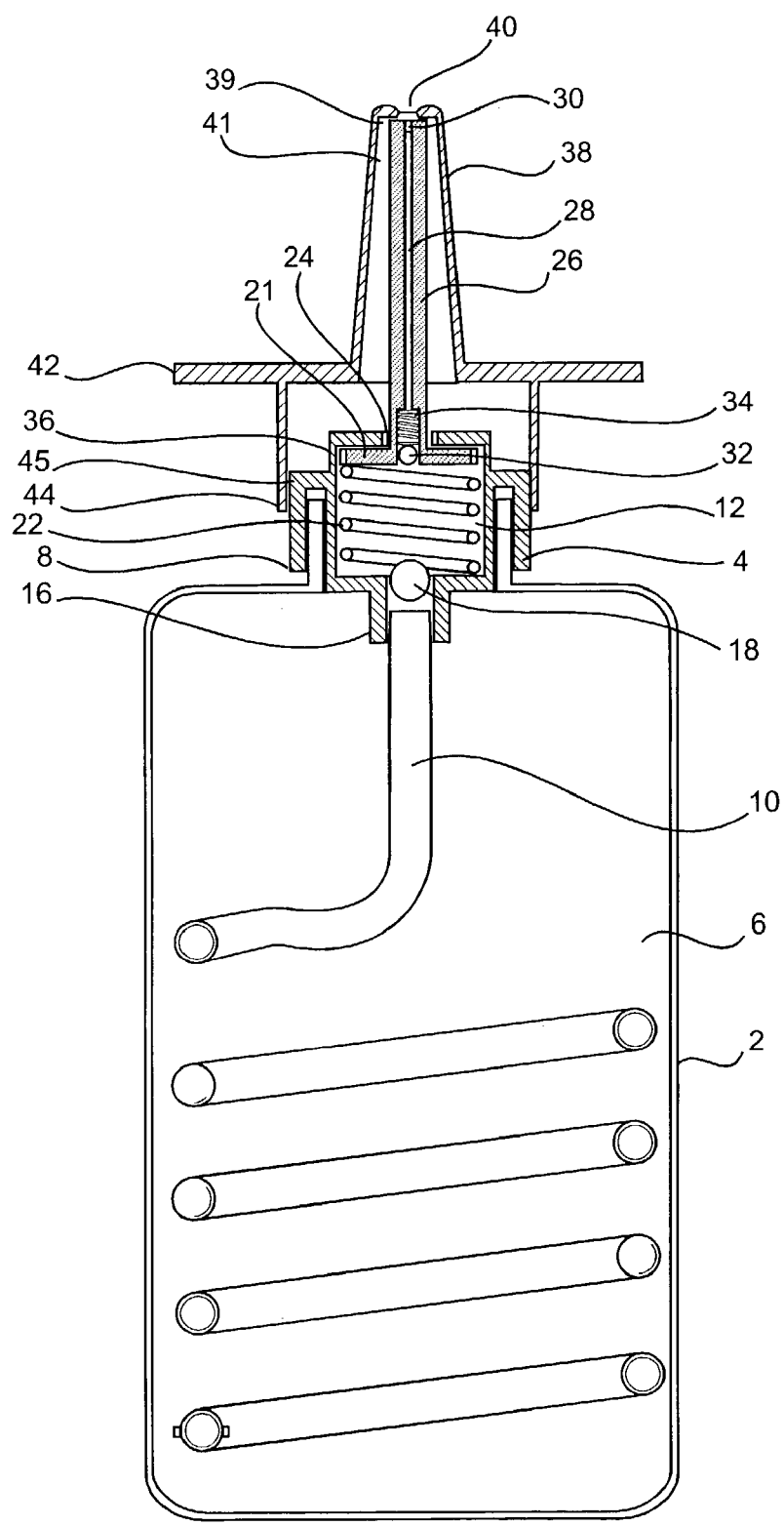
FIG. 3 is a schematic representation of the subject apparatus forming a first embodiment of the invention.
Figure 4:
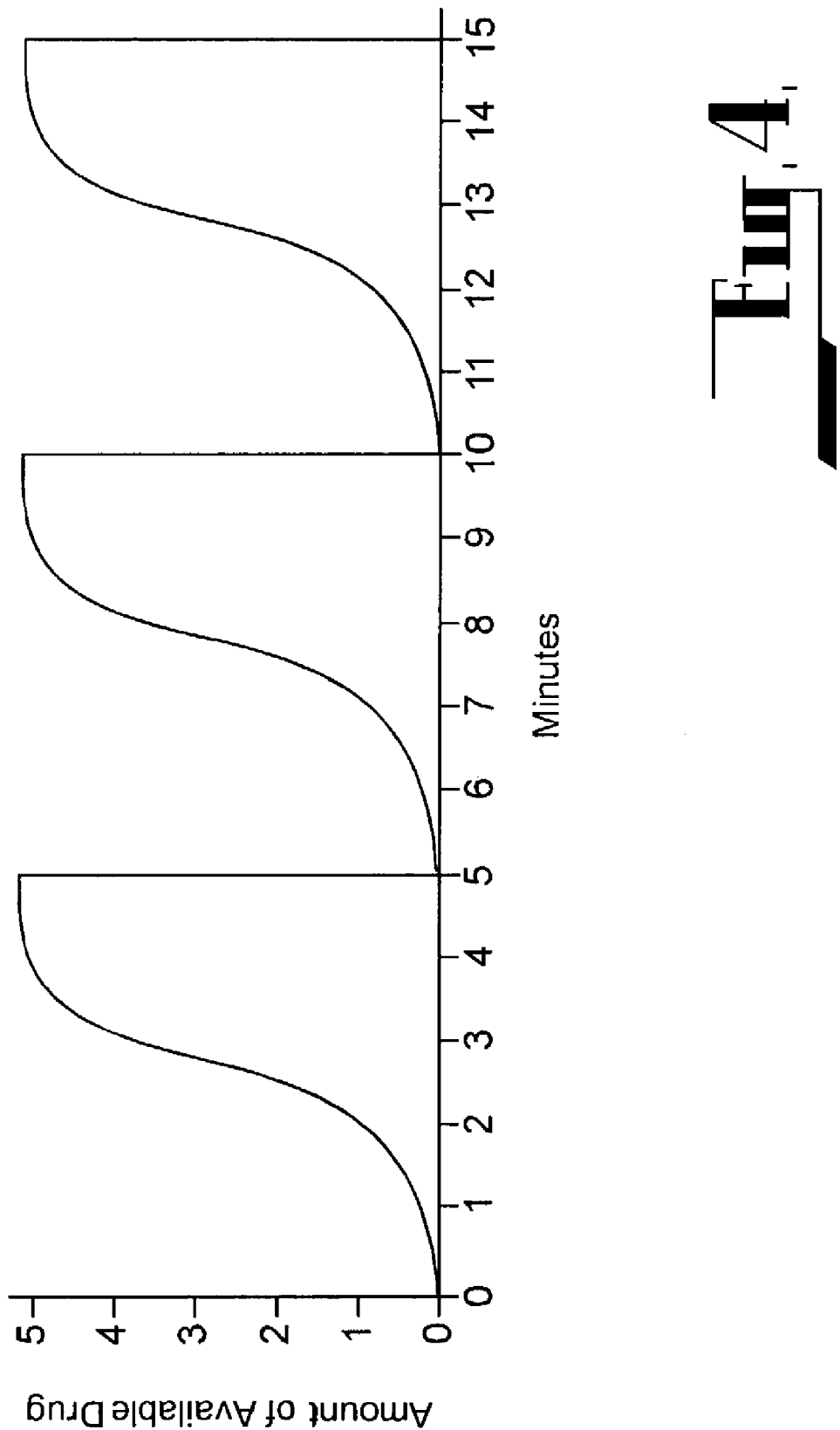
FIG. 4 shows the medicament availability curve for a 6 minute PCDD pump produced according to the present invention.

FIG. 3 illustrates one form of the present invention comprising a reservoir in the form of a bottle 2 which is releasably engaged with a pump 4 of a syringe type design. Within the reservoir there is a quantity of medicament 6, in liquid form, which is to be administered by the delivery device 8. The pump 4 is in communication with the reservoir 2 via a fine calibre tube 10 which restricts the flow rate of the medicament into the dose chamber 12. The fine calibre tube 10 releasably engages the base of the pumping means 14 by way of a connection joint 16. Interposed in the base of the pump housing 14 is an optional first one-way valve in the form of a ball valve 18. The ball valve prevents the passage of fluid through the fine calibre tubing 10 when a positive pressure is applied to the dose chamber.

Within the dose chamber there is a plunger 20 which is biased towards the top of the chamber 21 by a return spring 22. Extending perpendicular from the plunger, through an orifice 24 in the top of the chamber 21, is a plunger shaft 26. Through the central axis of the plunger 20 and plunger shaft 26 is a conduit 28 which provides a means for venting the medicament from the dose chamber when the plunger is depressed. The conduit 28 may also aid in atomising the medicament prior to release from the delivery device. At the distal end of the plunger shaft 30 the conduit 28 widens in diameter to facilitate dispersal of the medicament as it leaves the delivery device.

Interposed in the conduit is a controlling means 32 in the form of high pressure ball valve within an opening pressure of about 3000 mmHg. This valve prevents the influx of air into the dose chamber when the pump draws medicament from the reservoir and prevents the escape of fluid from the dose chamber when it is full. The valve comprises a seat and a ball above which is a spring which is biased towards sealing of the ball with the seat. When the plunger is depressed pressure is created in the dose chamber. When the pressure in the chamber exceeds the biasing force (eg 3000 mmHg) applied by the spring the valve opens, providing a passage through which medicament may flow.

Around the peripheral edge of the orifice 24, in the top of the chamber 21, there is a fluid seal 34 in sliding arrangement with the walls of the plunger shaft 26. The seal is capable of preventing the release of medicament and any vacuum formed within the chamber.

Around the plunger there is a second fluid seal 36 in sliding arrangement with the walls of the dose chamber. This seal is also capable of preventing the release of the medicament and any vacuum formed within the chamber. Sealing between the plunger and the chamber walls may be achieved using rubber or plastic gaskets.

Seated over the plunger shaft 26 is a sheath 38 which provides protection for the shaft. At the distal end of the sheath 37 there is at least a orifice 40 which allow release of the medicament from the delivery device. The sheath 38 extends down over the wall 41 of the plunger shaft and terminates above the top of the pump housing 14 at a height equivalent to the distance that the plunger travels downwards within the dose chamber when the plunger shaft is depressed. The sheath 38 then extends perpendicular from the shaft for a distance slightly greater than the horizontal width of the pump housing. The perpendicular extension 42 provides a means by which an external force applied by a user of the delivery device may be used to force the plunger shaft 26 downwards and hence drive the plunger 20 downwards within the dose chamber 12.

Protruding from beneath the perpendicular extension 42 is at least one projection 44. The projection 44 preferably envelopes part or all of the side walls of the pump housing 14 when the plunger is depressed. The projection may also aid as an engaging means between the sheath 38 and the pump housing 14. In this instance the peripheral rim 45 on the top of the pump housing may possess a flange (not shown) which engages an inverted flange (not shown) on the inner surface of the bottom of the projection, when the plunger is released.

In operation the user depresses the sheath 38 which in turn forces the plunger 20 downwards within the dose chamber 12 and creates a positive pressure within the chamber. The positive pressure forces the valve in the base of the pump housing to close and the controlling means 32 to open once a critical pressure had been reached. Depression of the plunger 20 within the dose chamber 12 causes a quantity of medicament 6 equal to the volume of the dose chamber to pass through the conduit 28 and out through orifice 40, releasing the medicament. When the sheath 38 is released the spring 22 in the dose chamber drives the plunger upwards towards the top of the dose chamber creating a vacuum within the chamber. The vacuum opens the first one-way valve 18 in the base of the pump and closes the controlling means 32 in the conduit 28 thereby enabling medicament to be drawn from the reservoir 2 through the fine calibre tubing 10 into the dose chamber 12. The rate at which the plunger is driven upwards towards the top of the dose chamber is determined by the rate of flow of medicament from the reservoir through the fine calibre tubing 10. The overall infusion rate into the dose chamber is thus controlled by the volume of the dose chamber and the flow resistance of the tube 10 in relation to the medicament.

The fine calibre tube 10 is preferably a plastics tube having a very narrow bore and a relatively thick wall, the latter ensuring that it does not kink in use. Such a tube and the method of producing it are described in published International Patent Application WO88/02637. The tube 10 preferably has a length in the range 10 to 700 mm and a lumen diameter in the range 0.001 inch (0.025 mm) to 0.008 inch (0.20 mm). In a particularly preferred form, the lumen diameter is 0.070 mm and the tube length is about 30 to 60 mm.

The use of fine bore tubing not only sets the refill time of the dose chamber 12, but also acts as a rate limiting factor in inhibiting over use of the delivery device by the patient. As an additional safety factor, the controlling means 32 located in the conduit 28 should have an opening pressure greater than the maximum possible hydrostatic pressure which is required to produce an appropriate spray.

An alternative form of a one-way valve may also be used in the delivery device. Instead of a ball-valve the valve may consist of at least two pieces of elastomeric material formed in an inverted cone, pyramid or V-shape. When a vacuum is applied to the apex of the valve mechanism the elastomeric material separates creating an opening through which medicament may flow. When a positive pressure is applied to the apex of the valve the elastomeric material is forced together closing the passage way.

FIG. 4 illustrates a series of medicament availability curves from a device produced according to the present invention. The curves each represent medicament availability over a 5 minute delivery schedule. During the first 2½ minutes of filling of the delivery device there is insufficient liquid in the dose chamber to facilitate release of the medicament. After 3 minutes there is an exponential increase in the availability of the medicament followed by a gradual peaking of medicament availability as the dose chamber becomes full. By modifying the opening pressure of the controlling means and the return pressure in the pump, it is possible to shift the availability of the medicament closer towards the optimum lockout time, (ie 5 minutes) in these graphs. The opening pressure of the controlling means must be balanced against the patient's ability to use the device.

Filling and medicament availability curves for a device produced according to the present invention have been developed and can be provided to the Examiner, including those that illustrate the filling rate of the dose chamber of the device, the availability of medicament, and the effective absorption of medicament as it is released from the device. Initially filling of the dose chamber is rapid yet relatively inaccessible because of the influence of the high pressure controlling means. As the dose chamber begins to reach a substantially full state the amount of medicament that may be released from the invention increases. However because the dose chamber is not entirely full there is insufficient pressure behind the medicament to drive it through the second conduit to disperse it upon release. Thus most of the released medicament quickly coalesces as a liquid which in the case of a nasal spray is incapable of reaching the tissue surface where absorption takes place. Consequently medicament absorption is minimal. As the dose chamber becomes completely full a spray may be generated when the device is activated. This in turn is capable of saturating the surface area of the tissue surrounding the point of medicament administration which is reflected in a rapid rise in the effective absorption of medicament as it is released from the device.

Figure 5:
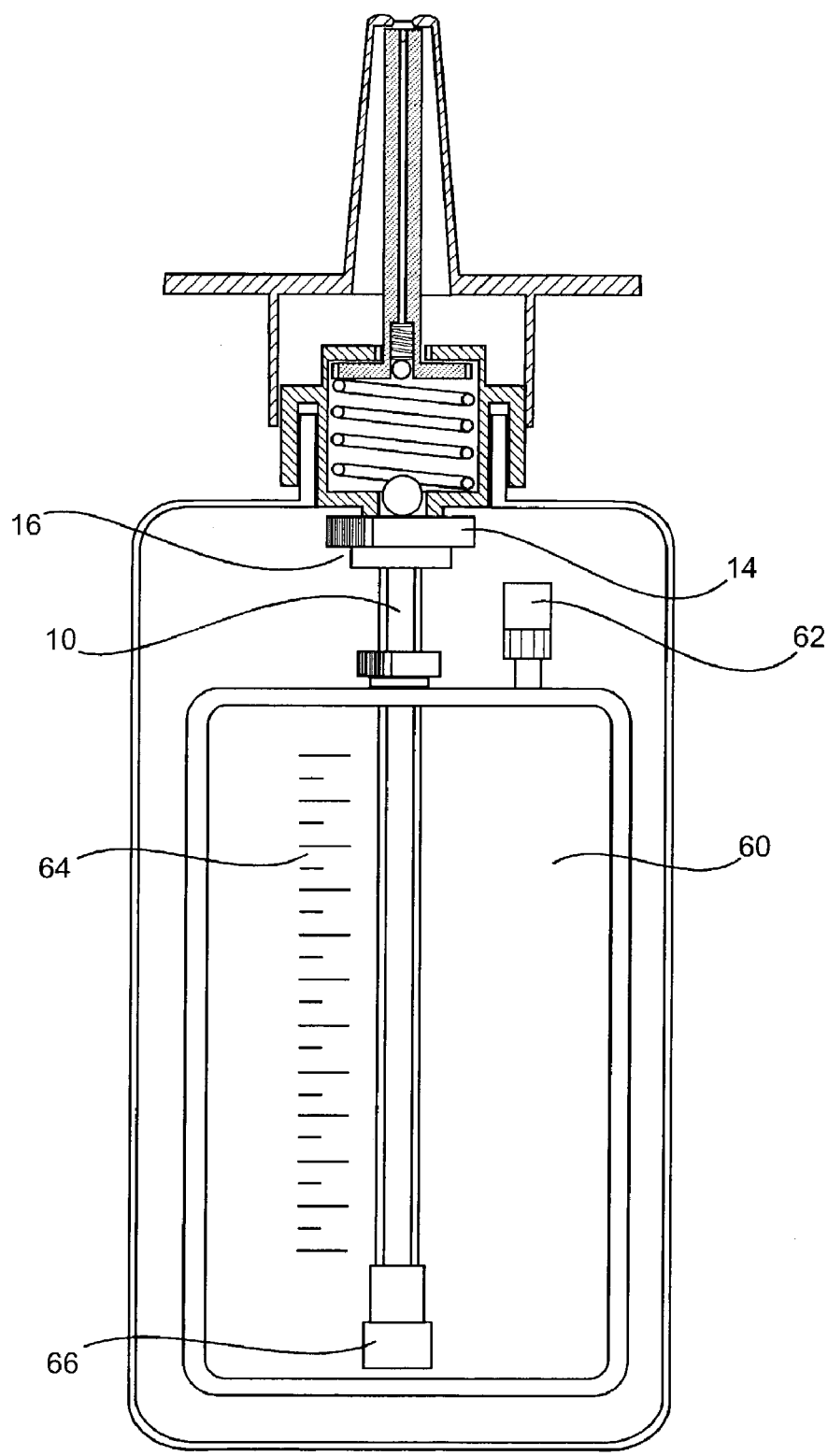
FIG. 5 is a schematic representation of the subject apparatus depicting an alternative form of the medicament reservoir.

FIG. 5 illustrates an alternative form of the medicament reservoir. In this form the medicament is contained within a collapsible sealed bag 60 which prevents entry of air into the fine calibre tubing when properly filled. The bag resides within the reservoir 2 and is connected to the pump housing 14 via a fine calibre tube 10. The tube 10 is releasably engaged to the pump housing via a connection joint 16.

To assist in re-use of the bag 60 there is provided a refilling port 62, where the bag can be filled or emptied by means of a standard hypodermic syringe. The bag also contains graduated markings 64 to indicate what volume of medicament is within the bag.

Attached to the open end of the fine calibre tube within the bag is a spacer 64 which prevents the collapsible bag from covering the opening of the tube.

Figure 6:
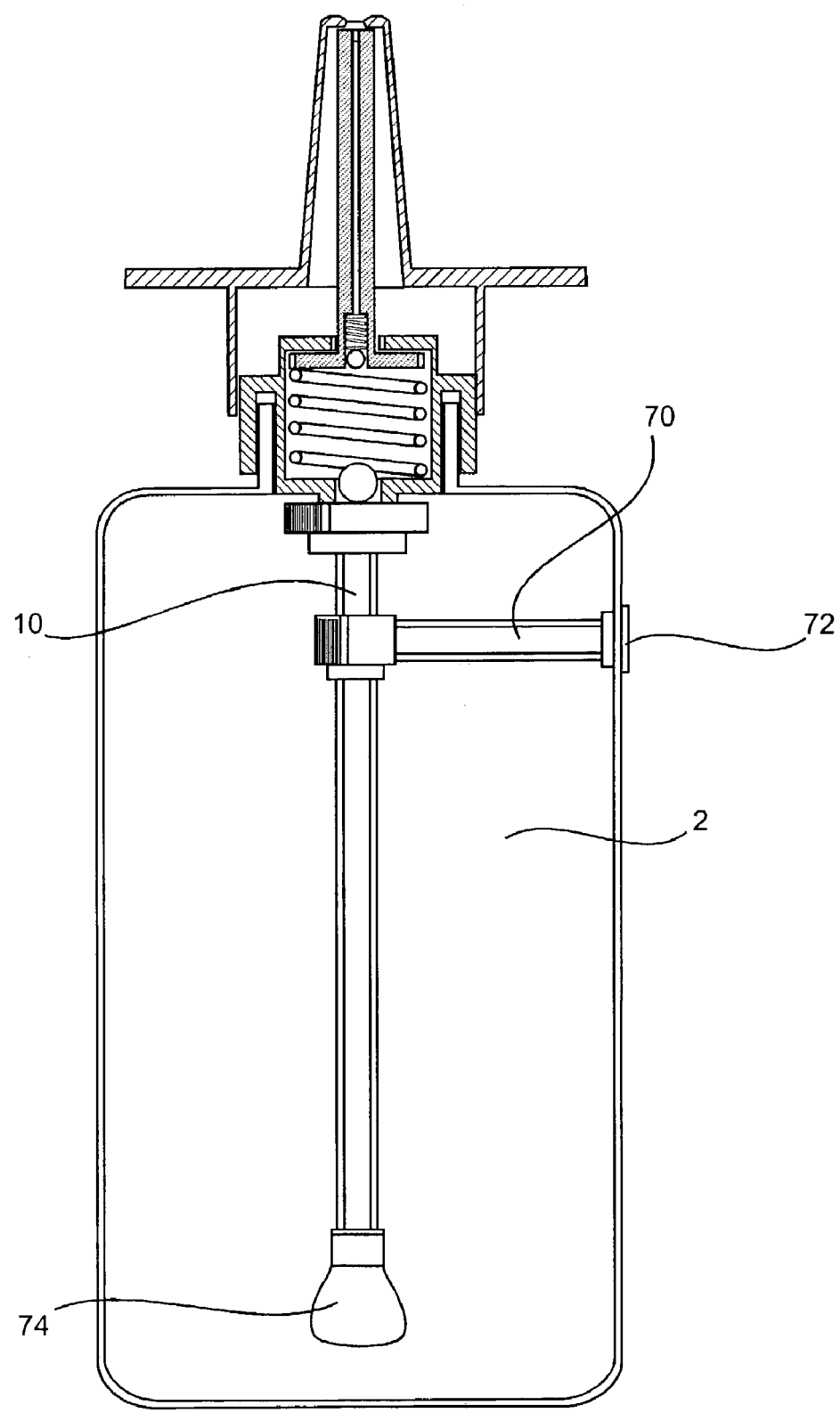
FIG. 6 is a schematic representation of the subject apparatus depicting yet another form of the medicament reservoir.

FIG. 6 illustrates a second form of the medicament reservoir. In this form the reservoir is provided with a fill line 70 terminating in an injection site 72 which allows priming of the fine calibre tubing 10 by means of a standard hypodermic syringe. A hydrophilic filter (sponge) 72 may be included in the fine calibre tubing or the fill line to prevent any air inadvertently introduced into the injection site 72 from reaching the reservoir 2.

Figure 7:
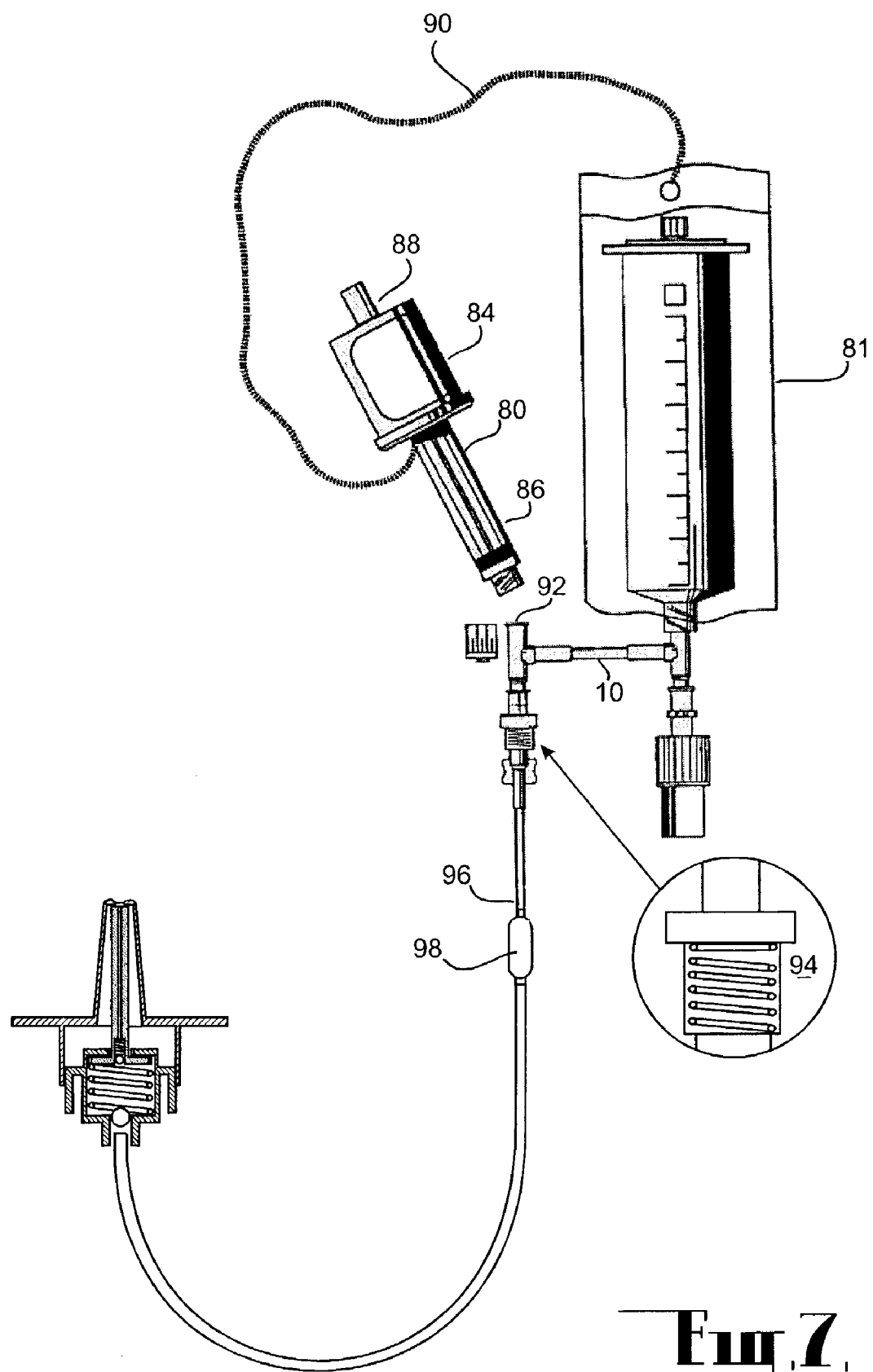
FIG. 7 is a schematic representation of the subject invention depicting a second alternative form of the reservoir wherein the reservoir is separated from the delivery device by a non-electronic pump system.

FIG. 7 illustrates a another form of the medicament reservoir. In this form there is provided between the reservoir 2 and the delivery device 8 a non-electronic pump system. In this embodiment the reservoir 2 is connected to a non-electronic manually operable pumping mechanism such as an aspirating syringe 80 via fine calibre tubing 10 which has a fine bore. In this embodiment the reservoir is enclosed within a transparent plastic bag 81 for reasons of safety and hygiene. The return spring (not shown) of the aspirating syringe 80 is housed within a cylindrical casing 84, the plunger 86 being actuated by a patient demand button 88 extending from the casing. The syringe and the bag are linked by a cord 90 which allows the apparatus to be hung around the patient's neck for ambulatory use.

An preferred feature is the ability to remove the syringe (or equivalent) to assist in priming the system. The fine calibre tubing 10 has such an extremely fine bore that it is difficult to force liquid through it from the reservoir 2 to prime the system. Accordingly to prime the system the aspiration syringe is removed from the connector 92 and the patient line is filled with medicament, which may be done by connecting a relatively large syringe at the connector and injecting this to overcome the resistance of the one way valve 94. The fine calibre tubing is also primed with liquid at this stage.

The aspirating syringe is then reapplied to the connector with the patient demand button 88 held down. On release of the patient demand button 88, fluid is drawn through the fine calibre tube 10 and is stored in the aspirating syringe 80. When the patient demand button 88 is depressed medicament is forced out of the syringe past the one way valve 94 and fills the delivery device line 96 within which there is interposed a non-elastic balloon 98. The balloon serves as a secondary reservoir from which the delivery device draws medicament.

Fine calibre tubing between the reservoir and the actuating syringe restricts the filling time of the syringe to the rate of flow of medicament through the tubing. Thus there is an induced time delay in the refilling of the syringe.

An preferred feature is the provision of a one way valve 94 between the actuating syringe 80 and the delivery device tubing 96 (illustrated as being of undefined length). Preferably this valve is activated under high pressure only. The pressure of actuation being equivalent to or slightly greater than the pressure generated by a vacuum at sea level (ie, greater than 760 mm of mercury). Thus the one way valve 94 serves as a lock out mechanism preventing premature release of liquid in the actuating syringe until the syringe is full.

The delivery device line 96 is not formed of fine calibre tubing, but of tubing of a suitable diameter that does not substantially restrict the flow of liquid into the dose chamber. In this form the delivery device may be actuated in rapid succession to deliver all of the medicament in the delivery device line 96 and the non-elastic balloon 98. However once the medicament in the delivery device line 96 and the non-elastic balloon 98 has been delivered, the patient is unable to obtain further medicament until the patent demand button 88 is depressed thereby forcing medicament across the one way valve 94. Release of the patient demand button causes the return spring within the cylindrical casing to return the plunger to rest position. This in turn creates a vacuum within the syringe and draws medicament across the flow control tubing 10.

Figure 8:
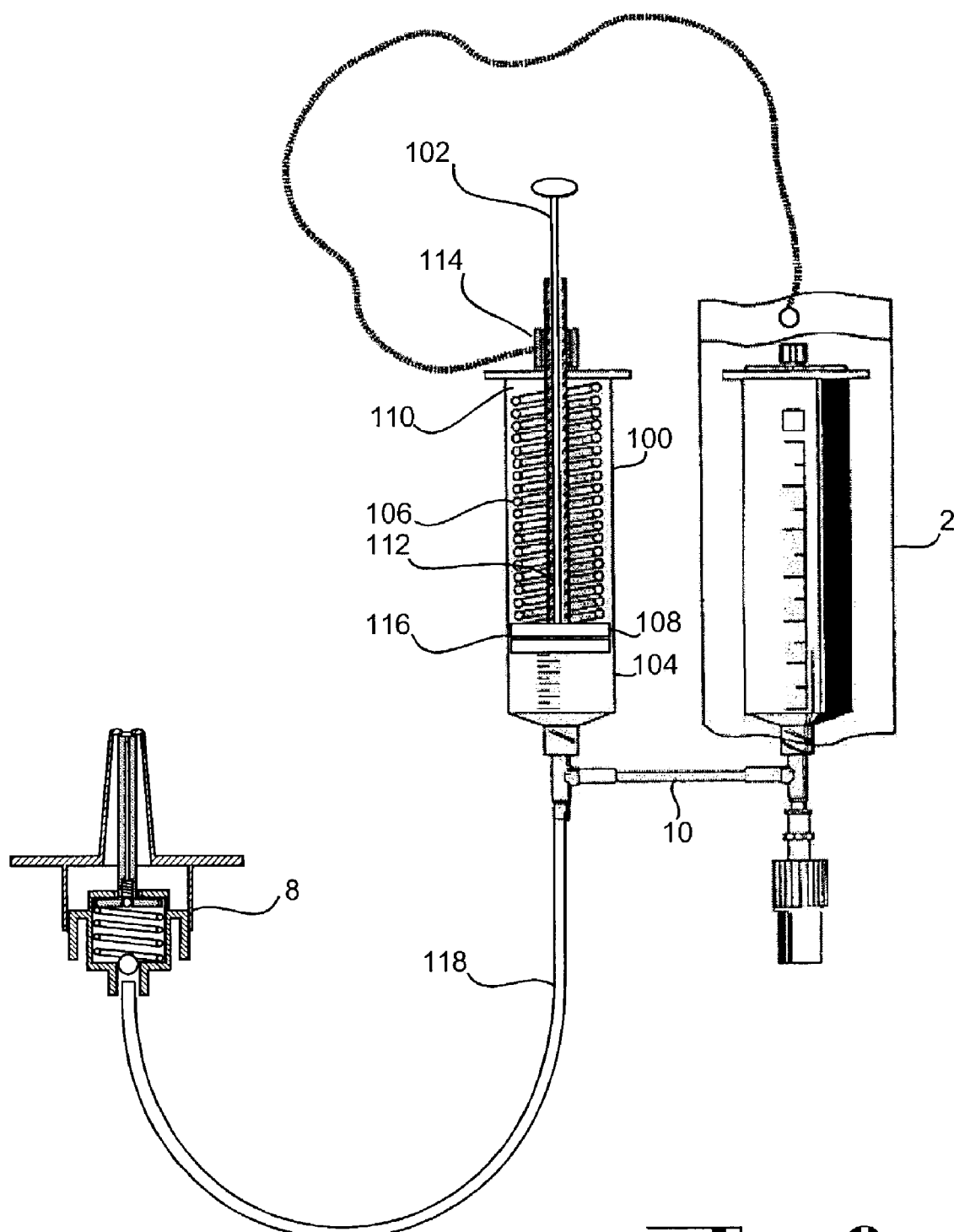
FIG. 8 is a schematic representation of the subject invention depicting a third alternative form of the reservoir wherein the reservoir is separated from the delivery device by a second reservoir system.

FIG. 8 illustrates a furtherembodiment of the medicament reservoir. In this form there is provided between the reservoir 2 and the delivery device 8 a second reservoir 100.

The reservoir 2 is enclosed with a transparent plastic bag for reasons of safety and hygiene. In this embodiment the reservoir is connected to the second reservoir 100 via flow control tubing 10 having a fine bore. Further the plastic bag containing the reservoir 102 is connected to a priming pin by a cord which prevents accidental loss of the pin when it is separated from the second reservoir 100.

Within the casing 104 of the second reservoir 100 there is a return spring 106 which is engaged to a plunger 108. The spring is also engaged to a first end 110 of the second reservoir. Passing centrally through the first end and the casing is an adjustable stopping means 112 which defines the maximum distance that the plunger 108 may be moved within the casing 104. Outside the second reservoir 100 above the first end is an adjustment means 114 which provides a system for adjusting the relative position of the stopping means within the second reservoir. The volume of liquid that may be drawn into the small reservoir may be adjusted by altering the distance of the first end 116 of the stopping means relative to the first end.

Passing centrally through the first end 110 and the stopping means 112 is a separable priming pin 102 which extends from above the adjustment means 114 to the first end 116 of the stopping means. When the priming pin is inserted into the second reservoir the first end of the pin abuts the plunger 108. Priming of the second reservoir may be achieved by depressing the priming pin thereby forcing the plunger towards the second end of the reservoir. This extends the biasing means. When the priming pin is released the contractile pressure created by the return spring draws the plunger 108 towards the first end 116 of the stopping means thereby drawing medicament into the second reservoir.

An important feature is the ability to remove the second reservoir 100 to assist in priming the system. The control tubing 10 has such an extremely fine bore that it is difficult to force liquid through it from the reservoir to prime the system. Accordingly, to prime the system the second reservoir is removed from the connector and the delivery device tubing 118 is filled with medicament, which may be done by connecting a relatively large syringe (not shown) at the connector and injecting medicament into the delivery device tubing 118 as well as the fine calibre tubing 10.

The second reservoir 100 is then reapplied to the connector while the priming pin 102 is held down. On release of the priming pin, fluid is drawn through the fine calibre tubing and is stored in the second reservoir. After release of the pin it may be removed from the second reservoir. Fine calibre tubing 10 between the reservoir 2 and the small reservoir 100 restricts the filling time of the second reservoir to the flow rate of medicament through the tubing.

An important aspect of this invention is the contractile tension of the return spring 106 in the second reservoir 100. Preferably the spring is capable of drawings of vacuum within the reservoir which is less than the vacuum drawn within the dose chamber in the delivery device. For example, the second reservoir 100 would be capable of generating a pressure of negative 400 mm Hg (compared to atmosphere).

Upon actuation of the delivery device 8 medicament is released from the dose chamber. The pump then draws a vacuum of greater than atmospheric pressure which fills the dose chambers using medicament in the delivery device line. Since the vacuum drawn by the delivery device is greater than that drawn by the second reservoir fluid will pass from the second reservoir into the delivery device. Once the dose chamber in the delivery device is full no further vacuum is drawn across the delivery device line. The second reservoir 100 continues to draw liquid through the small reservoir until the plunger 108 abuts the first end of the stopping means 116.

In this configuration a patient is able to rapidly deliver all of the medicament stored in the secondary reservoir but is prevented from drawing further medicament from that reservoir until the second reservoir gains sufficient fluid to refill the delivery device. The rate of filling the second reservoir is dictated by the flow rate across the flow control tubing. Thus if a patient delivers all of the medicament in the second reservoir in a number of rapid doses they will be locked out from obtaining additional medicament until there is sufficient medicament in the second reservoir to refill and activate the delivery device.

Figure 9:
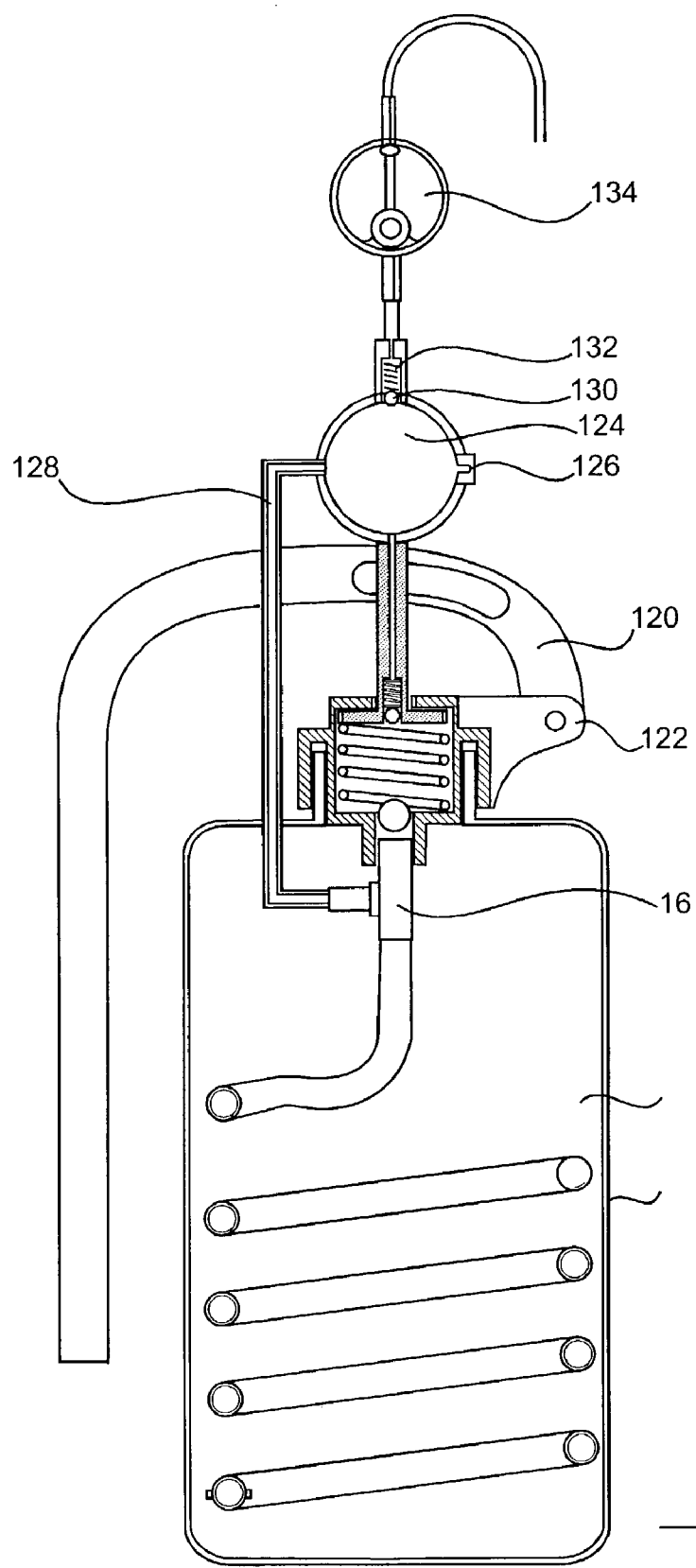
FIG. 9 is a schematic illustration of the subject apparatus depicting a further embodiment of the present invention.

FIG. 9 illustrates an alternative embodiment of the present invention. In this form there is provided a secondary discharge control assembly attached to the delivery device 8 and reservoir 2. The delivery device 8 comprises a modified pump actuating means consisting of a lever 120 which is pivotally mounted to the pump housing on a mount 122. The lever engages the plunger shaft in a manner which facilitates slidable engagement between the lever and the shaft (not shown). When the lever is depressed it drives the shaft through the pump housing thereby forcing actuation of the pumping assembly.

Releasably mounted to the distal end of the plunger shaft is a second dose chamber 124. Located within the second dose chamber housing is a venting system 126, a return line 128 and a release portal 130 within which is located a pressure activated controlling means 132. The release portal is connected to an intravenous delivery line which in turn is connected to a patient.

The venting system 126 is adapted to release any air trapped within the second dose chamber and which may enter the chamber follow discharge of medicament into said chamber The return line 128 passes from the second dose chamber and is in fluid communication with the reservoir 2 where it meets connection joint 16. Excess medicament passing through the return line is thus recirculated into the operational filling of the dose chamber 12.

The pressure activated controlling means 132 is in the form of a ball valve. The valve prevents the flow of medicament from the delivery line into the second dose chamber. It also provides a means of restricting the passage of medicament through the delivery line, at least, until sufficient pressure is generated by the fluid entering the second dose chamber to open the valve. Thus be selecting suitable valves to act as the pressure activated controlling means it is possible to restrict the passage of fluid entering the delivery line to that which has come from a full dose chamber.

Upon activation of the pumping assembly, medicament is forced into the second dose chamber 124 via the conduit 28. If the pressure generated by medicament entering the second dose chamber is sufficient to open the pressure activated controlling means 132 it will enter the delivery and pass via an air filter 134 to a patient. If however, there is insufficient pressure behind the medicament delivered to the second dose chamber the pressure activated controlling means will remain closed and no liquid will enter the delivery line. Excess liquid retained in the second dose chamber may be returned to the reservoir 2 via the return line 128.

The invention thus provides a patient-controlled apparatus which is of simple and inexpensive construction and has a high level of inherent safety. The apparatus is extremely simple to operate. Owing to its simplicity and cheapness it can be used as a disposable item. The apparatus can be manufactured for use with a particular medicament by suitable choice of delivery device and bore of the fine calibre tube; on-site adjustment is then not required, and the apparatus can be used by a patient without specialist training.

Figure 10A:
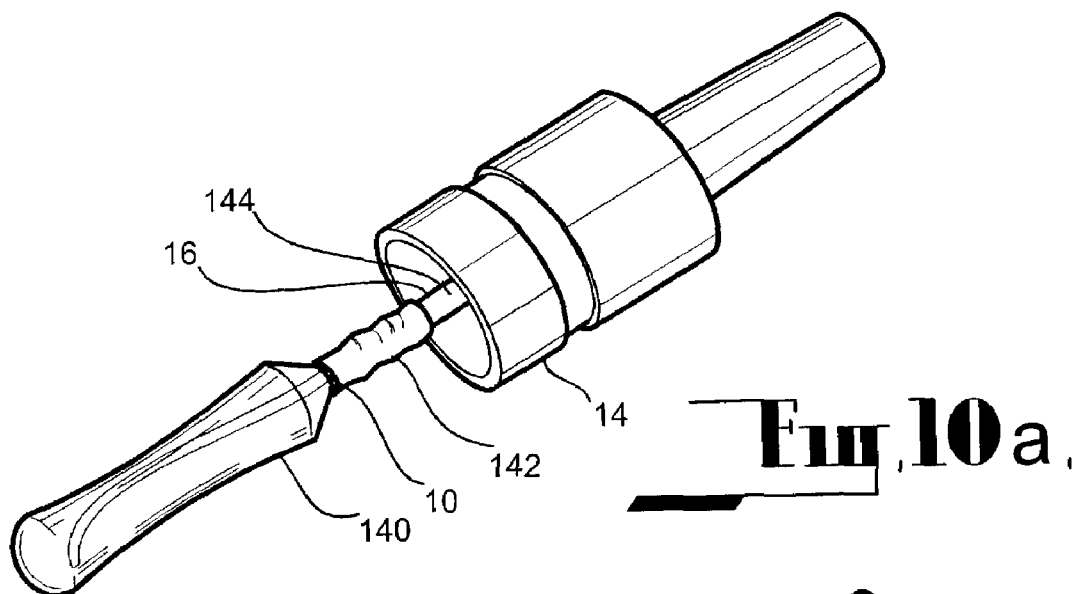
FIG. 10a shows a collapsible bag attached to the end of the nasal spray suction tubing and the pump housing.

FIG. 10a illustrates a delivery device comprising a reservoir in the form of a deformable bag 140 containing medicament that is releasably engaged to the pump 4. Located within the deformable bag 140 is a conduit 10 that is engaged (releasably) to the connection joint 16 located at the base of the pumping means 14. Releasable engagement between the connection joint and the conduit may be enhanced by means of a crimping cap 142, which when crimped bites both the conduit and the connection joint forming a secure sealing between these two component. Between the connection joint 16 and the dose chamber there is a fluid passage 144, which provides an avenue through which fluid may pass to enter the dose chamber. When present, the fluid passage 144 may contain a one way valve (not shown) allowing the passage of fluid from the deformable bag 140 into the dose chamber while prohibiting the reverse flow of fluid.

Figure 10B:
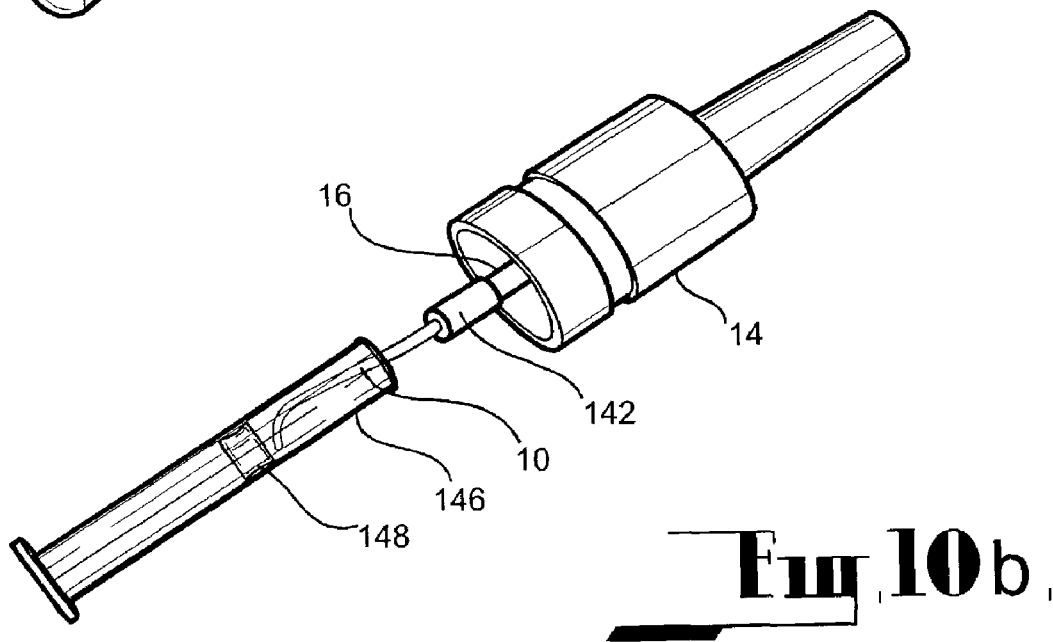
FIG. 10b shows a syringe that allows the plunger to move as the fluid is evacuated.

FIG. 10b illustrates an alternative embodiment which shows the reservoir as a a syringe 146 comprising a plunger 148 which is drawn towards base of the syringe 150 as fluid is withdrawn or evacuated.

Figure 11:
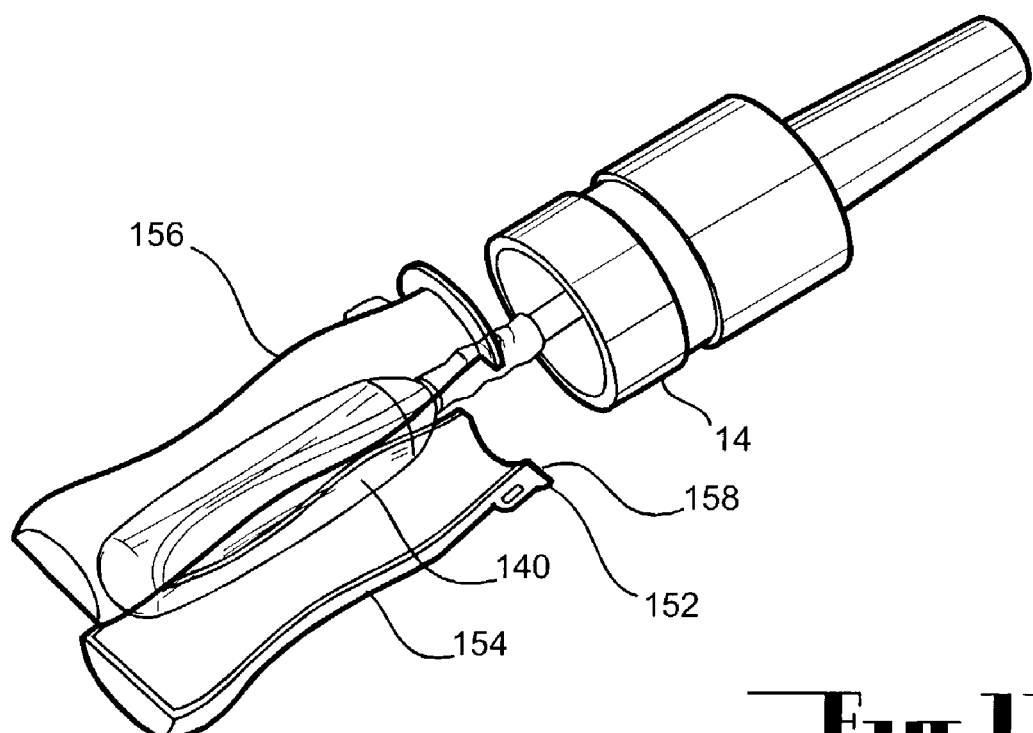
FIG. 11 shows the assembly of a rigid container around a collapsible bag

In a preferred form the deformable bag 140 is protected by a removable housing 152 which cloaks the bag. FIG. 11 illustrates a separable housing comprising two halves 154 and 156 each possessing a relatively narrow-neck with a flanged wide brim 158 located at the end of the housing 160 which engages the pump means 14. When the housing is brought in contact with the pump housing the wide brimmed flange provides a means to sealingly engage the housing with the pumping means. This may be achieved by the use of glue or like fixing means.

Figure 12:
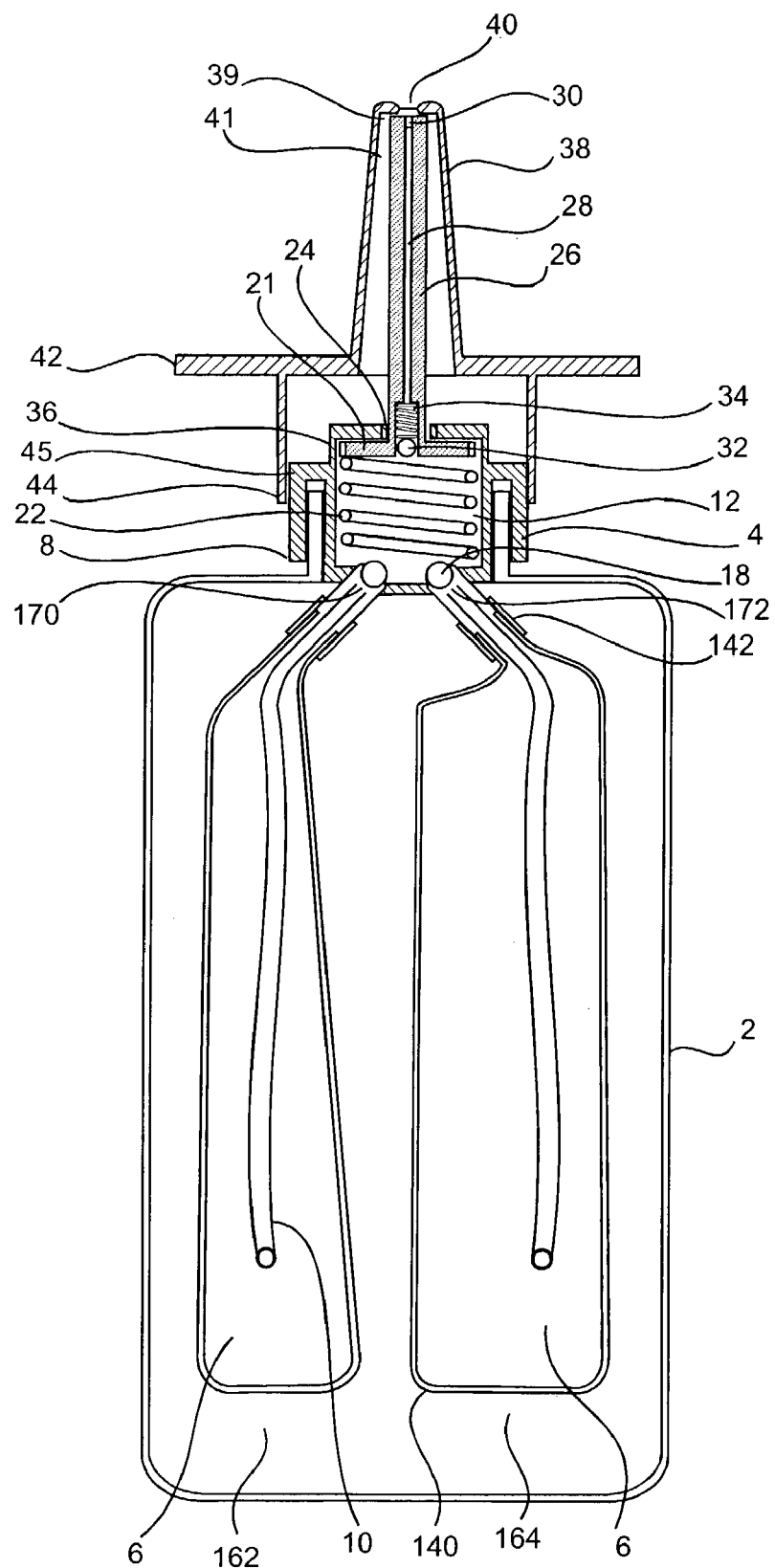
FIG. 12 illustrates a delivery device as illustrated in figure three except the device is adapted to withdraw fluid from more than a single reservoir.

FIG. 12 illustrates a delivery device as described above except that the device is fitted with two reservoirs 162 and 164. Extending from each reservoir is a separate conduit 166 and 168 which engage distinct connection joints 170 and 172 located at the base of the pump housing. In an alternate form of the invention each conduit may fuse together prior to the connection joint, such that the pump housing is fitted with only one connection joint (not shown).

Figure 13:
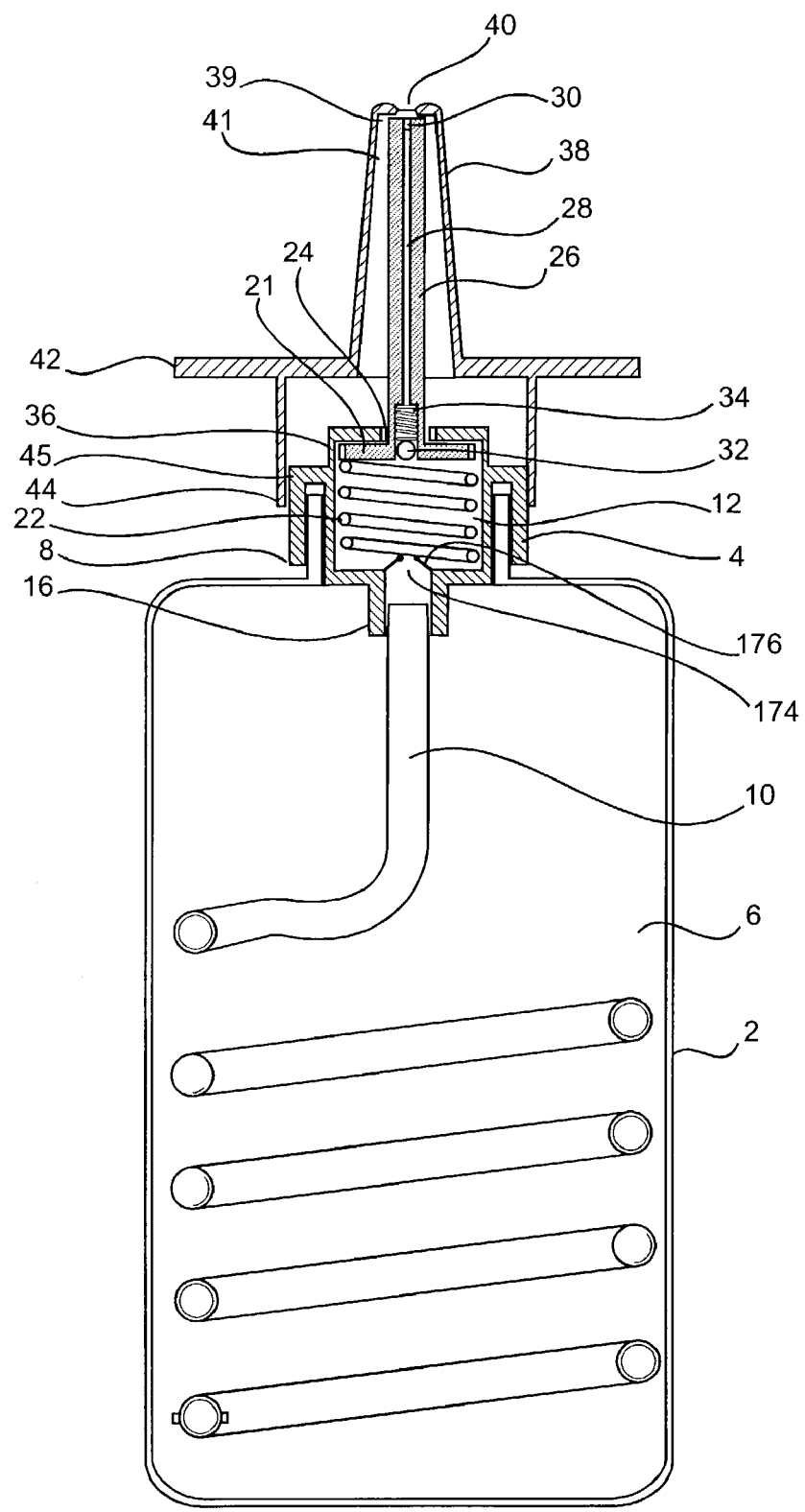
FIG. 13 illustrates a delivery device as illustrated in figure three except the device is modified through the removal of the one-way valve.

FIG. 13 illustrates a patient controlled delivery device of the type described in FIG. 3 except that the one-way valve has been removed and the portal 174 through which fluid flows as it enters the dose chambers is fitted with a flange 176 adapted to retard the reverse flow of medicament upon actuation of the pump means.

Experiments conducted using the device described in FIG. 3 comprising nasal Fentanyl as the medicament have demonstrated that when a 50 μg solution is delivered with the described device the amount of spray that can be tolerated by most patients is limited to 0.2 ml. This limits the spray delivered to 91 μg, which proved to be insufficient for most patients with severe pain. Patients having severe pain typically required 120-180 μg of Fentanyl in order to control their pain. If however a solution of 300 μg of Fentanyl per ml is delivered using the device good control of pain may be achieved within three sprays. By using a lock-out of three to five minutes the device may be used to relieve the pain for the majority of patients inside a 10 minute period.

Therefore when Fentanyl is used in the subject device it is necessary to ensure that the concentration of the solution placed in the reservoir is at least 150 μg per ml and preferably close to a range of 300 μg per ml plus or minus 150 μg per ml. This provides a clinically useful solution when one is using 0.2 μg spray volume. When the spray volume is reduced then the concentration of the solution can be adjusted to maintain the same dose levels.

Fentanyl concentrated at 150-450 μg per ml is therefore excellent for nasal administration with a 0.2 ml spray. With patients using a 0.1 ml nasal spray the solution should preferably be in the order of 300-900 μg of Fentanyl per ml. These solutions have not been used clinically in this way before.

When the medicament used in the device is nasal Hydromorphine a solution of 50 μg per ml has been found effect, while 30 mg per ml solutions of nasal Morphine sulphate or nasal Dimorphine have also been found to be effective.

Further, nasal Remifentanil with a short lock-out of one to two minutes is specifically useful in labour and in other situations where there is significant pain. A very short lockout of one to two minutes has not previously been used extensively and with the spray device described herein is specifically useful for safety reasons with Remifantanil.

The invention claimed is:

1. A delivery device for patient-controlled infusion of a medicament, the delivery device comprising:
   (i) a reservoir for the medicament, which reduces in volume as medicament is withdrawn from the reservoir; and
   (ii) a pump which has a predetermined delivery dose, wherein the pump comprises at least a first conduit which connects the reservoir to a pump chamber, a one-way valve in fluid communication with the first conduit and the pump chamber which permits medicament flow into the chamber but prevents reverse flow there from, a second conduit extending from the pump chamber and having a distal end through which the medicament may be released, and a controlling means in fluid communication with said pump chamber and said second conduit, wherein:
   (a) the first conduit is a fine calibre tube, which is capable of restricting the filling time of the pump chamber to greater than 1 minute, and is suitably adapted to restrict the flow of medicament into the chamber to a predetermined maximum delivery rate;
   (b) the controlling means:
      (i) opens when pressure within the pump chamber exceeds a pre-selected minimum opening pressure, said opening pressure being greater than 760 mmHg;
      (ii) is adapted to prevent the reverse flow of medicament and air into the pump chamber; and
   (c) the second conduit is adapted to release the medicament in the form of a spray; wherein after expulsion of medicament from the pump chamber a working interrelationship is formed between the fine calibre tubing and the controlling means to generate a lockout phase during which a patient is unable to effectively access a dose of medicament being drawn into the pump chamber until said chamber contains sufficient medicament to aid in treating said patient.

2. A delivery device according to claim 1, wherein the reservoir is a collapsible bag.

3. A delivery device according to claim 2, wherein the collapsible bag is made from any suitable material that preferably does not absorb significant quantities of lipaphyllic drugs used with the delivery device, such as polyethylene.

4. A delivery device according to claim 1 wherein the reservoir is a syringe with plunger that reduces in volume as the fluid is removed.

5. A delivery device according to claim 1 wherein the controlling means is biased towards the closed position by a resilient biasing means.

6. A delivery device according to claim 5 wherein the controlling means has an opening pressure in the range of from 760 mmHg to about 5000 mmHg.

7. A delivery device according to claim 6 wherein the controlling means has an opening a pressure of from 1000 mmHg to about 3500 mmHg.

8. A delivery device according to claim 5 wherein the controlling means has an opening a pressure of 3000 mmHg.

9. A delivery device according to claim 1 wherein the controlling means has a high opening pressure but a low pressure threshold to remain open.

10. A delivery device according to claim 1 wherein there is at least a means for reducing the medicament to fine particles as it passes through the second conduit.

11. A delivery device according to claim 1 wherein the medicament is pumped under high pressure through and along the side walls of the second conduit, preferably in a rotary action.

12. A delivery device according to claim 11 wherein the second conduit narrows at its distal end so that fluid rotating around the conduit increases its centrifugal rotation as it converges on the distal end of the conduit.

13. A delivery device according to claim 1 wherein the pumping means is releasably engaged to the first conduit and may be separated from the first conduit to allow the first conduit to be filled with priming liquid.

14. A delivery device according to claim 1 wherein the reservoir is collapsible bag or syringe with plunger which is adapted to engaged the pump by means of a dismountable connection and which is capable of holding the first conduit.

15. A delivery device according to claim 1 wherein the reservoir has one or more means for introducing a medicament into the reservoir chamber.

16. A delivery device according to claim 1 wherein the reservoir is provided with at least a means for trapping gases inadvertently introduced into reservoir.

17. A delivery device according to claim 1 wherein the reservoir is separated from the delivery device by a fluid control system, comprising:
   (i) a second reservoir which holds at least two medicament doses and which is located between the end of the flow control tubing and the delivery device;
   (ii) a fluid delivery means interposed between the reservoir and the second reservoir; and
   (iii) a high pressure activated valve with an opening pressure above atmospheric pressure which is interposed between the fluid delivery means and the second reservoir, wherein the fluid delivery means is capable of drawing medicament through the flow control tubing, is capable of holding a volume of medicament equivalent to the volume held by the second reservoir and is capable of delivering that medicament across the a high pressure activated valve to the second reservoir.

18. A delivery device according to claim 17 wherein the opening pressure of the high pressure activated valve is greater than 800 mmHg.

19. A delivery device according to claim 1 wherein there is provided a secondary delivery control assembly which is releasably engaged to the second conduit, and which comprises
   (i) a second delivery chamber
   (ii) a return tube to the reservoir which extends from the second delivery chamber to the reservoir and
   (iii) an intravenous delivery line, wherein the housing of the second delivery chamber contains at least an air filter to remove trapped air and a delivery portal, which is connected to the intravenous delivery line.

20. A delivery device according to claim 1 wherein the reservoir contains more than one medicament.

21. A delivery device according to claim 20 wherein the medicaments are a lipophylic drug and a hydrophilic blocker.

22. A delivery device according to claim 1 having a chain or string may be attached.

23. A delivery device according to claim 1 having a counter to record dosage administration.

24. A delivery device for patient-controlled infusion of a medicament, the delivery device comprising:
   (i) at least a first and second reservoir for medicament storage; and
   (ii) a pump which has a predetermined delivery dose, wherein the pump comprises a separate conduit feeding into each reservoir to connect said reservoir to the pump chamber, a one-way valve in fluid communication with each conduit extending from the reservoir and the pump chamber which permits medicament flow into the chamber but prevents reverse flow there from, a second conduit extending from the pump chamber and having a distal end through which the medicament may be released, and a controlling means in fluid communication with said pump chamber and said second conduit, wherein:
   (a) each conduit connecting the reservoir to the dose chamber is a fine calibre tube, which is capable of restricting the filling time of the pump chamber to greater than 1 minute, and is suitably adapted to restrict the flow of medicament into the chamber to a predetermined maximum delivery rate;
   (b) the controlling means:
      (i) opens when pressure within the pump chamber exceeds a pre-selected minimum opening pressure, said opening pressure being greater than 760 mmHg;
      (ii) is adapted to prevent the reverse flow of medicament and air into the pump chamber; and
   (c) the second conduit is adapted to release the medicament in the form of a spray; wherein after expulsion of medicament from the pump chamber a working interrelationship is formed between the fine calibre tubing and the controlling means to generate a lockout phase during which a patient is unable to effectively access a dose of medicament being drawn into the pump chamber until said chamber contains sufficient medicament to aid in treating said patient.

25. A delivery device for patient-controlled infusion of a medicament, the delivery device comprising:
   (i) at least a first reservoir for medicament storage; and
   (ii) a pump which has a predetermined delivery dose, wherein the pump comprises a conduit feeding from each reservoir to connect said reservoir to the pump chamber, a second conduit extending from the pump chamber and having a distal end through which the medicament may be released, and a controlling means in fluid communication with said pump chamber and said second conduit, wherein:
   (a) Each conduit connecting the reservoir to the dose chamber is a fine calibre tube, which is capable of restricting the filling time of the pump chamber to greater than 1 minute, and is suitably adapted to restrict the flow of medicament into the chamber to a predetermined maximum delivery rate;
   (b) the controlling means:
      (i) opens when pressure within the pump chamber exceeds a pre-selected minimum opening pressure, said opening pressure being greater than 760 mmHg;
      (i) is adapted to prevent the reverse flow of medicament and air into the pump chamber; and
   (c) the second conduit is adapted to release the medicament in the form of a spray; wherein after expulsion of medicament from the pump chamber a working interrelationship is formed between the fine calibre tubing and the controlling means to generate a lockout phase during which a patient is unable to effectively access a dose of medicament being drawn into the pump chamber until said chamber contains sufficient medicament to aid in treating said patient.

* * * * *